US008187809B2

(12) United States Patent
Takata et al.

(10) Patent No.: US 8,187,809 B2
(45) Date of Patent: May 29, 2012

(54) METHOD FOR JUDGING LYMPH NODE METASTASIS OF STOMACH CANCER AND KIT USED THEREFOR

(75) Inventors: Hideki Takata, Kobe (JP); Takayuki Takahata, Kobe (JP); Kazuki Nakabayashi, Kobe (JP); Kayo Shoji, Kobe (JP); Yasuhiro Otomo, Kobe (JP)

(73) Assignee: Sysmex Corporation, Hyogo (JP)

( * ) Notice: Subject to any disclaimer, the term of this patent is extended or adjusted under 35 U.S.C. 154(b) by 350 days.

(21) Appl. No.: 11/972,943

(22) Filed: Jan. 11, 2008

(65) Prior Publication Data

US 2008/0182259 A1 Jul. 31, 2008

(30) Foreign Application Priority Data

Jan. 15, 2007 (JP) ................................ 2007-005900

(51) Int. Cl.
*C12Q 1/68* (2006.01)
*C07H 21/04* (2006.01)

(52) U.S. Cl. ..................... 435/6.11; 435/6.12; 435/6.14; 536/24.3

(58) Field of Classification Search ........................ None
See application file for complete search history.

(56) References Cited

U.S. PATENT DOCUMENTS

2007/0264635 A1 11/2007 Suzuki et al.

FOREIGN PATENT DOCUMENTS

JP 2005-304497 A 11/2005
WO 2005/001126 A1 1/2005

OTHER PUBLICATIONS

Whitehead, Andrew et al. Variation in tissue specific gene expression amoung natural populations. 2005 Genome Biology vol. 6 Article R13.*

Hoshikawa, Yasushi et al. Hypoxia induces different genes in the lungs of rats compared with mice. 2003. Physiol Genomics vol. 12 pp. 209-219.*

Thisted, Ronald. What is a P value. 1998. The University of Chicago found online at http://www.stat.uchicago.edu/~thisted.*

Chan, Eric. Integrating Transcriptomics and Proteomics. G&P magazine 2006 vol. 6 No. 3 pp. 20-26.*

K. Kubota et al., Quantitative detection of micrometastases in the lymph nodes of gastric cancer patients with real-time RT-PCR, a comparative study with immunohistochemistry, International Journal of Cancer, May 20 2003, pp. 136-143, vol. 105, No. 1.

Hiromichi Sonoda et al., Detection of lymph node micrometastasis in pN0 early gastric cancer: Efficacy of duplex RT-PCR with MUC2 and TFF1 in mucosal cancer, Oncology Reports 16, 2006, pp. 411-416.

* cited by examiner

*Primary Examiner* — Amanda Shaw
(74) *Attorney, Agent, or Firm* — Sughrue Mion, PLLC

(57) ABSTRACT

The present invention provides a novel marker capable of accurately diagnosing the lymph node metastasis of stomach cancer. An mRNA, or a fragment thereof, coding for at least one protein selected from TFF1, AGR2, PRSS8, MUC1, MUC4 and MUC17 can be useful as a lymph node metastasis marker.

7 Claims, 2 Drawing Sheets

SEQUENCE LISTING

<160> NUMBER OF SEQ ID NOS: 30

<210> SEQ ID NO 1
<211> LENGTH: 20
<212> TYPE: DNA
<213> ORGANISM: Artificial
<220> FEATURE:
<223> OTHER INFORMATION: Primer

<400> SEQUENCE: 1
ccctggtgct tctatcctaa 20

<210> SEQ ID NO 2
<211> LENGTH: 20
<212> TYPE: DNA
<213> ORGANISM: Artificial
<220> FEATURE:
<223> OTHER INFORMATION: Primer

<400> SEQUENCE: 2
cagatccctg cagaagtgtc 20

<210> SEQ ID NO 3
<211> LENGTH: 21
<212> TYPE: DNA
<213> ORGANISM: Artificial
<220> FEATURE:
<223> OTHER INFORMATION: Primer

<400> SEQUENCE: 3
attcttgctc cttgtggccc t 21

<210> SEQ ID NO 4
<211> LENGTH: 22
<212> TYPE: DNA
<213> ORGANISM: Artificial
<220> FEATURE:
<223> OTHER INFORMATION: Primer

<400> SEQUENCE: 4
atgagttggt caccccaacc tc 22

<210> SEQ ID NO 5
<211> LENGTH: 19
<212> TYPE: DNA
<213> ORGANISM: Artificial
<220> FEATURE:
<223> OTHER INFORMATION: Primer

<400> SEQUENCE: 5
ttccctgatg gcctttgga 19

<210> SEQ ID NO 6
<211> LENGTH: 21
<212> TYPE: DNA
<213> ORGANISM: Artificial
<220> FEATURE:
<223> OTHER INFORMATION: Primer

<400> SEQUENCE: 6
cccaaaaagc acacccagaa g 21

<210> SEQ ID NO 7
<211> LENGTH: 22
<212> TYPE: DNA

<213> ORGANISM: Artificial
<220> FEATURE:
<223> OTHER INFORMATION: Primer

<400> SEQUENCE: 7
cccagtctcc tttcctcctg ct 22

<210> SEQ ID NO 8
<211> LENGTH: 22
<212> TYPE: DNA
<213> ORGANISM: Artificial
<220> FEATURE:
<223> OTHER INFORMATION: Primer

<400> SEQUENCE: 8
gccgaagtct ccttttctcc ac 22

<210> SEQ ID NO 9
<211> LENGTH: 21
<212> TYPE: DNA
<213> ORGANISM: Artificial
<220> FEATURE:
<223> OTHER INFORMATION: Primer

<400> SEQUENCE: 9
ccaccaactt catcgccttt g 21

<210> SEQ ID NO 10
<211> LENGTH: 22
<212> TYPE: DNA
<213> ORGANISM: Artificial
<220> FEATURE:
<223> OTHER INFORMATION: Primer

<400> SEQUENCE: 10
cgtcttcatg gtcaggctga aa 22

<210> SEQ ID NO 11
<211> LENGTH: 21
<212> TYPE: DNA
<213> ORGANISM: Artificial
<220> FEATURE:
<223> OTHER INFORMATION: Primer

<400> SEQUENCE: 11
aggcctcagg taatgacgac a 21

<210> SEQ ID NO 12
<211> LENGTH: 21
<212> TYPE: DNA
<213> ORGANISM: Artificial
<220> FEATURE:
<223> OTHER INFORMATION: Primer

<400> SEQUENCE: 12
agttcccatg gaaggctctc a 21

<210> SEQ ID NO 13
<211> LENGTH: 24
<212> TYPE: DNA
<213> ORGANISM: Artificial
<220> FEATURE:
<223> OTHER INFORMATION: Primer

<400> SEQUENCE: 13
ccatgtatcc tgatgttccc attg 24

<210> SEQ ID NO 14
<211> LENGTH: 25
<212> TYPE: DNA
<213> ORGANISM: Artificial
<220> FEATURE:
<223> OTHER INFORMATION: Primer

<400> SEQUENCE: 14
gcactgaacg ttgatctcgt agttg 25

<210> SEQ ID NO 15
<211> LENGTH: 22
<212> TYPE: DNA
<213> ORGANISM: Artificial
<220> FEATURE:
<223> OTHER INFORMATION: Primer

<400> SEQUENCE: 15
cttcctgtgc aagtaccgac ca 22

<210> SEQ ID NO 16
<211> LENGTH: 23
<212> TYPE: DNA
<213> ORGANISM: Artificial
<220> FEATURE:
<223> OTHER INFORMATION: Primer

<400> SEQUENCE: 16
tgagcagatt tagccaggct agc 23

<210> SEQ ID NO 17
<211> LENGTH: 22
<212> TYPE: DNA
<213> ORGANISM: Artificial
<220> FEATURE:
<223> OTHER INFORMATION: Primer

<400> SEQUENCE: 17
agacaatcac agtctctgcg ga 22

<210> SEQ ID NO 18
<211> LENGTH: 20
<212> TYPE: DNA
<213> ORGANISM: Artificial
<220> FEATURE:
<223> OTHER INFORMATION: Primer

<400> SEQUENCE: 18
atccttgtcc tccacgggtt 20

<210> SEQ ID NO 19
<211> LENGTH: 20
<212> TYPE: DNA
<213> ORGANISM: Artificial
<220> FEATURE:
<223> OTHER INFORMATION: Primer

<400> SEQUENCE: 19
cagatcgaag gcctgaagga 20

<210> SEQ ID NO 20
<211> LENGTH: 19
<212> TYPE: DNA
<213> ORGANISM: Artificial
<220> FEATURE:
<223> OTHER INFORMATION: Primer

<400> SEQUENCE: 20

```
cttggcccct cagcgtact                                                19
```

<210> SEQ ID NO 21
<211> LENGTH: 22
<212> TYPE: DNA
<213> ORGANISM: Artificial
<220> FEATURE:
<223> OTHER INFORMATION: Primer

<400> SEQUENCE: 21

```
cattgacagt gttgcccaga tg                                            22
```

<210> SEQ ID NO 22
<211> LENGTH: 25
<212> TYPE: DNA
<213> ORGANISM: Artificial
<220> FEATURE:
<223> OTHER INFORMATION: Primer

<400> SEQUENCE: 22

```
aaagacctag ctctcctcaa aaagg                                         25
```

<210> SEQ ID NO 23
<211> LENGTH: 22
<212> TYPE: DNA
<213> ORGANISM: Artificial
<220> FEATURE:
<223> OTHER INFORMATION: Primer

<400> SEQUENCE: 23

```
tcctcaccct gaagtacccc at                                            22
```

<210> SEQ ID NO 24
<211> LENGTH: 22
<212> TYPE: DNA
<213> ORGANISM: Artificial
<220> FEATURE:
<223> OTHER INFORMATION: Primer

<400> SEQUENCE: 24

```
agccacacgc agctcattgt ag                                            22
```

<210> SEQ ID NO 25
<211> LENGTH: 508
<212> TYPE: DNA
<213> ORGANISM: Homo sapiens

<400> SEQUENCE: 25

```
atccctgact cggggtcgcc tttggagcag agaggaggca atggccacca tggagaacaa     60

ggtgatctgc gccctggtcc tggtgtccat gctggccctc ggcaccctgg ccgaggccca    120

gacagagacg tgtacagtgg ccccccgtga aagacagaat tgtggttttc ctggtgtcac    180

gccctcccag tgtgcaaata agggctgctg tttcgacgac accgttcgtg gggtcccctg    240

gtgcttctat cctaatacca tcgacgtccc tccagaagag gagtgtgaat tttagacact    300

tctgcaggga tctgcctgca tcctgacgcg gtgccgtccc cagcacggtg attagtccca    360

gagctcggct gccacctcca ccggacacct cagacacgct tctgcagctg tgcctcggct    420

cacaacacag attgactgct ctgactttga ctactcaaaa ttggcctaaa aattaaaaga    480

gatcgatatt aaaaaaaaaa aaaaaaaa                                       508
```

<210> SEQ ID NO 26

<211> LENGTH: 1701
<212> TYPE: DNA
<213> ORGANISM: Homo sapiens

<400> SEQUENCE: 26

```
ccgcatccta gccgccgact cacacaaggc aggtgggtga ggaaatccag agttgccatg      60

gagaaaattc cagtgtcagc attcttgctc cttgtggccc tctcctacac tctggccaga     120

gataccacag tcaaacctgg agccaaaaag gacacaaagg actctcgacc caaactgccc     180

cagaccctct ccagaggttg ggtgaccaa ctcatctgga ctcagacata tgaagaagct     240

ctatataaat ccaagacaag caacaaaccc ttgatgatta ttcatcactt ggatgagtgc     300

ccacacagtc aagctttaaa gaaagtgttt gctgaaaata aagaaatcca gaaattggca     360

gagcagtttg tcctcctcaa tctggtttat gaaacaactg acaaacacct ttctcctgat     420

ggccagtatg tccccaggat tatgtttgtt gacccatctc tgacagttag agccgatatc     480

actggaagat attcaaatcg tctctatgct tacgaacctg cagatacagc tctgttgctt     540

gacaacatga agaaagctct caagttgctg aagactgaat tgtaaagaaa aaaaatctcc     600

aagcccttct gtctgtcagg ccttgagact tgaaaccaga agaagtgtga gaagactggc     660

tagtgtggaa gcatagtgaa cacactgatt aggttatggt ttaatgttac aacaactatt     720

ttttaagaaa aacaagtttt agaaatttgg tttcaagtgt acatgtgtga aaacaatatt     780

gtatactacc atagtgagcc atgattttct aaaaaaaaaa ataaatgttt tgggggtgtt     840

ctgttttctc caacttggtc tttcacagtg gttcgtttac caaataggat taaacacaca     900

caaaatgctc aaggaaggga caagacaaaa ccaaaactag ttcaaatgat gaagaccaaa     960

gaccaagtta tcatctcacc acaccacagg ttctcactag atgactgtaa gtagacacga    1020

gcttaatcaa cagaagtatc aagccatgtg ctttagcata aaagaatatt tagaaaaaca    1080

tcccaagaaa atcacatcac tacctagagt caactctggc caggaactct aaggtacaca    1140

ctttcattta gtaattaaat tttagtcaga ttttgcccaa cctaatgctc tcagggaaag    1200

cctctggcaa gtagctttct ccttcagagg tctaatttag tagaaaggtc atccaaagaa    1260

catctgcact cctgaacaca ccctgaagaa atcctgggaa ttgaccttgt aatcgatttg    1320

tctgtcaagg tcctaaagta ctggagtgaa ataaattcag ccaacatgtg actaattgga    1380

agaagagcaa agggtggtga cgtgttgatg aggcagatgg agatcagagg ttactagggt    1440

ttaggaaacg tgaaaggctg tggcatcagg gtaggggagc attctgccta acagaaatta    1500

gaattgtgtg ttaatgtctt cactctatac ttaatctcac attcattaat atatggaatt    1560

cctctactgc ccagcccctc ctgatttctt tggcccctgg actatggtgc tgtatataat    1620

gctttgcagt atctgttgct tgtcttgatt aacttttttg gataaaacct tttttgaaca    1680

gaaaaaaaaa aaaaaaaaaa a                                              1701
```

<210> SEQ ID NO 27
<211> LENGTH: 1938
<212> TYPE: DNA
<213> ORGANISM: Homo sapiens

<400> SEQUENCE: 27

```
gactttggtg gcaagaggag ctggcggagc ccagccagtg ggcggggcca ggggaggggc      60

gggcaggtag gtgcagccac tcctgggagg accctgcgtg gccagacggt gctggtgact     120

cgtccacact gctcgcttcg gatactccag gcgtctcccg ttgcggccgc tccctgcctt     180

agaggccagc cttggacact tgctgcccct ttccagcccg gattctggga tccttccctc     240
```

```
tgagccaaca tctgggtcct gccttcgaca ccaccccaag gcttcctacc ttgcgtgcct    300

ggagtctgcc ccaggggccc ttgtcctggg ccatggccca gaagggggtc ctggggcctg    360

ggcagctggg ggctgtggcc attctgctct atcttggatt actccggtcg gggacaggag    420

cggaaggggc agaagctccc tgcggtgtgg ccccccaagc acgcatcaca ggtggcagca    480

gtgcagtcgc cggtcagtgg ccctggcagg tcagcatcac ctatgaaggc gtccatgtgt    540

gtggtggctc tctcgtgtct gagcagtggg tgctgtcagc tgctcactgc ttccccagcg    600

agcaccacaa ggaagcctat gaggtcaagc tgggggccca ccagctagac tcctactccg    660

aggacgccaa ggtcagcacc ctgaaggaca tcatccccca ccccagctac ctccaggagg    720

gctcccaggg cgacattgca ctcctccaac tcagcagacc catcaccttc tcccgctaca    780

tccggcccat ctgcctccct gcagccaacg cctccttccc caacggcctc cactgcactg    840

tcactggctg gggtcatgtg gccccctcag tgagcctcct gacgcccaag ccactgcagc    900

aactcgaggt gcctctgatc agtcgtgaga cgtgtaactg cctgtacaac atcgacgcca    960

agcctgagga gccgcacttt gtccaagagg acatggtgtg tgctggctat gtggaggggg   1020

gcaaggacgc ctgccagggt gactctgggg gcccactctc ctgccctgtg gagggtctct   1080

ggtacctgac gggcattgtg agctggggag atgcctgtgg ggcccgcaac aggcctggtg   1140

tgtacactct ggcctccagc tatgcctcct ggatccaaag caaggtgaca gaactccagc   1200

ctcgtgtggt gccccaaacc caggagtccc agcccgacag caacctctgt ggcagccacc   1260

tggccttcag ctctgcccca gcccagggct tgctgaggcc catccttttc ctgcctctgg   1320

gcctggctct gggcctcctc tccccatggc tcagcgagca ctgagctggc cctacttcca   1380

ggatggatgc atcacactca aggacaggag cctggtcctt ccctgatggc ctttggaccc   1440

agggcctgac ttgagccact ccttccttca ggactctgcg ggaggctggg gccccatctt   1500

gatctttgag cccattcttc tgggtgtgct tttgggacc atcactgaga gtcaggagtt   1560

ttactgcctg tagcaatggc cagagcctct ggcccctcac ccaccatgga ccagcccatt   1620

ggccgagctc ctggggagct cctgggaccc ttggctatga aaatgagccc tggctcccac   1680

ctgtttctgg aagactgctc ccggcccgcc tgcccagact gatgagcaca tctctctgcc   1740

ctctccctgt gttctgggct ggggccacct ttgtgcagct tcgaggacag gaaaggcccc   1800

aatcttgccc actggccgct gagcgccccc gagccctgac tcctggactc cggaggactg   1860

agcccccacc ggaactgggc tggcgcttgg atctggggtg ggagtaacag ggcagaaatg   1920

attaaaatgt ttgagcac                                                 1938
```

```
<210> SEQ ID NO 28
<211> LENGTH: 1209
<212> TYPE: DNA
<213> ORGANISM: Homo sapiens

<400> SEQUENCE: 28

acctctcaag cagccagcgc ctgcctgaat ctgttctgcc ccctccccac ccatttcacc     60

accaccatga caccgggcac ccagtctcct ttcttcctgc tgctgctcct cacagtgctt    120

acagttgtta cgggttctgg tcatgcaagc tctaccccag gtggagaaaa ggagacttcg    180

gctacccaga gaagttcagt gcccagctct actgagaaga atgctttgtc tactggggtc    240

tctttctttt tcctgtcttt tcacatttca aacctccagt ttaattcctc tctggaagat    300

cccagcaccg actactacca agagctgcag agagacattt ctgaaatgtt tttgcagatt    360

tataaacaag gggttttct gggcctctcc aatattaagt tcaggccagg atctgtggtg    420
```

```
gtacaattga ctctggcctt ccgagaaggt accatcaatg tccacgacgt ggagacacag    480

ttcaatcagt ataaaacgga agcagcctct cgatataacc tgacgatctc agacgtcagc    540

gtgagtgatg tgccatttcc tttctctgcc cagtctgggg ctggggtgcc aggctggggc    600

atcgcgctgc tggtgctggt ctgtgttctg gttgcgctgg ccattgtcta tctcattgcc    660

ttggctgtct gtcagtgccg ccgaaagaac tacgggcagc tggacatctt tccagcccgg    720

gatacctacc atcctatgag cgagtacccc acctaccaca cccatgggcg ctatgtgccc    780

cctagcagta ccgatcgtag cccctatgag aaggtttctg caggtaatgg tggcagcagc    840

ctctcttaca caaacccagc agtggcagcc acttctgcca acttgtaggg gcacgtcgcc    900

cgctgagctg agtggccagc cagtgccatt ccactccact caggttcttc agggccagag    960

cccctgcacc ctgtttgggc tggtgagctg ggagttcagg tgggctgctc acagcctcct   1020

tcagaggccc caccaatttc tcggacactt ctcagtgtgt ggaagctcat gtgggcccct   1080

gagggctcat gcctgggaag tgttgtggtg gggctccca ggaggactgg cccagagagc    1140

cctgagatag cggggatcct gaactggact gaataaaacg tggtctccca ctgcgccaaa   1200

aaaaaaaaa                                                           1209
```

```
<210> SEQ ID NO 29
<211> LENGTH: 7381
<212> TYPE: DNA
<213> ORGANISM: Homo sapiens

<400> SEQUENCE: 29

tacagcccca aggtcgctcc ctctggggcc ctttcttccc cattcttccc agcagcccaa     60

agctctggtg ggacaggggc agcccctggg gagggaggag aggacccagg aacccggcta    120

ggagggtggc ccacccattt ccagtgtgac ctgttcccat tcccccatgt ctcctcccat    180

ccctcccgcc actcagctca ggctgatgag aagcagagca acgggtgtat cggtgttttc    240

tttcctggtg gggtagtggg gtggggctga ggagagaaaa gggtgattag cgtggggccc    300

cgccctcttt tgtcctcttc ccaggttccc tggccccttc ggagaaacgc acttggttcg    360

ggccagccgc ctgaggggac gggctcacgt ctgctcctca cactgcagct gctgggccgt    420

ggagcttccc cagggagcca gggggacttt tgccgcagcc atgaaggggg cacgctggag    480

gagggtcccc tgggtgtccc tgagctgcct gtgtctctgc ctccttccgc atgtggtccc    540

aggaaccaca gaggacacat taataactgg aagtaaaact cctgccccag tcacctcaac    600

aggctcaaca acagcgacac tagagggaca atcaactgca gcttcttcaa ggacctctaa    660

tcaggacata tcagcttcat ctcagaacca ccagactaag agcacggaga ccaccagcaa    720

agctcaaacc gacaccctca cgcagatgat gacatcaact ctttttcttt ccccaagtgt    780

acacaatgtg atggagactg ttacgcagga gacagctcct ccagatgaaa tgaccacatc    840

atttccctcc agtgtcacca acacactcat gatgacatca aagactataa caatgacaac    900

ctccacagac tccactcttg gaaacacaga agagacatca acagcaggaa ctgaaagttc    960

taccccagtg acctcagcag tctcaataac agctggacag gaaggacaat cacgaacaac   1020

ttcctggagg acctctatcc aagacacatc agcttcttct cagaaccact ggactcggag   1080

cacgcagacc accagggaat ctcaaaccag caccctaaca cacagaacca cttcaactcc   1140

ttctttctct ccaagtgtac acaatgtgac agggactgtt tctcagaaga catctccttc   1200

aggtgaaaca gctacctcat ccctctgtag tgtcacaaac acatccatga tgacatcaga   1260

gaagataaca gtgacaacct ccacaggctc cactcttgga aacccagggg agacatcatc   1320
```

-continued

```
agtacctgtt actggaagtc ttatgccagt cacctcagca gccttagtaa cagttgatcc   1380
agaaggacaa tcaccagcaa ctttctcaag gacttctact caggacacaa cagctttttc   1440
taagaaccac cagactcaga gcgtggagac caccagagta tctcaaatca acaccctcaa   1500
caccctcaca ccggttacaa catcaactgt tttatcctca ccaagtggat tcaacccaag   1560
tggaacagtt tctcaggaga cattcccttc tggtgaaaca accatctcat ccccttccag   1620
tgtcagcaat acattcctgg taacatcaaa ggtgttcaga atgccaatct ccagagactc   1680
tactcttgga aacacagagg agacatcact atctgtaagt ggaaccattt ctgcaatcac   1740
ttccaaagtt tcaaccatat ggtggtcaga cactctgtca acagcactct cccccagttc   1800
tctacctcca aaaatatcca cagctttcca cacccagcag agtgaaggtg cagagaccac   1860
aggacggcct catgagagga gctcattctc tccaggtgtg tctcaagaaa tatttactct   1920
acatgaaaca acaacatggc cttcctcatt ctccagcaaa ggccacacaa cttggtcaca   1980
aacagaactg ccctcaacat caacaggtgc tgccactagg cttgtcacag gaaatccatc   2040
tacaagggca gctggcacta ttccaagggt cccctctaag gtctcagcaa taggggaacc   2100
aggagagccc accacatact cctcccacag cacaactctc ccaaaaaacaa caggggcagg   2160
cgcccagaca caatggacac aagaaacggg gaccactgga gaggctcttc tcagcagccc   2220
aagctatagt gtgattcaga tgataaaaac ggccacatcc ccatcttctt cacctatgct   2280
ggatagacac acatcacaac aaattacaac ggcaccatca acaaatcatt caacaataca   2340
ttccacaagc acctctcctc aggaatcacc agctgtttcc caaaggggtc acactcgagc   2400
cccgcagacc acacaagaat cacaaaccac gaggtccgtc tcccccatga ctgacaccaa   2460
gacagtcacc accccaggtt cttccttcac agccagtggg cactcgccct cagaaattgt   2520
tcctcaggac gcacccacca taagtgcagc aacaaccttt gccccagctc ccaccgggaa   2580
tggtcacaca acccaggccc cgaccacagc actgcaggca gcacccagca gccatgatgc   2640
caccctgggg ccctcaggag gcacgtcact ttccaaaaca ggtgccctta ctctggccaa   2700
ctctgtagtg tcaacaccag gggcccaga aggacaatgg acatcagcct ctgccagcac   2760
ctcacctgac acagcagcag ccatgaccca tacccaccag gctgagagca cagaggcctc   2820
tggacaaaca cagaccagcg aaccggcctc ctcagggtca cgaaccacct cagcgggcac   2880
agctacccct tcctcatccg ggcgagtgg cacaacacct tcaggaagcg aaggaatatc   2940
cacctcagga gagacgacaa ggttttcatc aaacccctcc agggacagtc acacaaccca   3000
gtcaacaacc gaattgctgt ccgcctcagc cagtcatggt gccatcccag taagcacagg   3060
aatggcgtct tcgatcgtcc ccggcacctt tcatcccacc ctctctgagg cctccactgc   3120
agggagaccg acaggacagt caagcccaac ttctcccagt gcctctcctc aggagacagc   3180
cgccatttcc cggatggccc agactcagag gacaggaacc agcagagggt ctgacactat   3240
cagcctggcg tcccaggcaa ccgacacctt ctcaacagtc ccacccacac ctccatcgat   3300
cacatccagt gggcttacat ctccacaaac ccagacccac actctgtcac cttcagggtc   3360
tggtaaaacc ttcaccacgg ccctcatcag caacgccacc cctcttcctg tcaccagcac   3420
ctcctcagcc tccacaggtc acgccacccc tcttgctgtc agcagtgcta cctcagcttc   3480
cacagtatcc tcggactccc ctctgaagat ggaaacatca ggaatgacaa caccgtcact   3540
gaagacagac ggtgggagac gcacagccac atcaccaccc cccacaacct cccagaccat   3600
catttccacc attcccagca ctgccatgca cacccgctcc acagctgccc ccatccccat   3660
cctgcctgag agaggagttt ccctcttccc ctatggggca ggcgccgggg acctggagtt   3720
```

```
cgtcaggagg accgtggact tcacctcccc actcttcaag ccggcgactg gcttccccct   3780
tggctcctct ctccgtgatt ccctctactt cacagacaat ggccagatca tcttcccaga   3840
gtcagactac cagatttttct cctaccccaa cccactccca acaggcttca caggccggga  3900
ccctgtggcc ctggtggctc cgttctggga cgatgctgac ttctccactg gtcgggggac   3960
cacattttat caggaatacg agacgttcta tggtgaacac agcctgctag tccagcaggc   4020
cgagtcttgg attagaaaga tgacaaacaa cgggggctac aaggccaggt gggccctaaa   4080
ggtcacgtgg gtcaatgccc acgcctatcc tgcccagtgg accctcggga gcaacaccta   4140
ccaagccatc ctctccacgg acgggagcag gtcctatgcc ctgtttctct accagagcgg   4200
tgggatgcag tgggacgtgg cccagcgctc aggcaacccg gtgctcatgg gcttctctag   4260
tggagatggc tatttcgaaa acagcccact gatgtcccag ccagtgtggg agaggtatcg   4320
ccctgataga ttcctgaatt ccaactcagg cctccaaggg ctgcagttct acaggctaca   4380
ccgggaagaa aggcccaact accgtctcga gtgcctgcag tggctgaaga gccagcctcg   4440
gtggcccagc tggggctgga accaggtctc ctgcccttgt tcctggcagc agggacgacg   4500
ggacttacga ttccaacccg tcagcatagg tcgctggggc ctcggcagta ggcagctgtg   4560
cagcttcacc tcttggcgag gaggcgtgtg ctgcagctac gggccctggg gagagtttcg   4620
tgaaggctgg cacgtgcagc gtccttggca gttggcccag gaactggagc cacagagctg   4680
gtgctgccgc tggaatgaca agccctacct ctgtgccctg taccagcaga ggcggcccca   4740
cgtgggctgt gctacataca ggcccccaca gcccgcctgg atgttcgggg acccccacat   4800
caccaccttg gatggtgtca gttacacctt caatgggctg gggacttcc tgctggtcgg    4860
ggcccaagac gggaactcct ccttcctgct tcagggccgc accgcccaga ctggctcagc   4920
ccaggccacc aacttcatcg cctttgcggc tcagtaccgc tccagcagcc tgggccccgt   4980
cacggtccaa tggctccttg agcctcacga cgcaatccgt gtcctgctgg ataaccagac   5040
tgtgacattt cagcctgacc atgaagacgg cggaggccag gagacgttca acgccaccgg   5100
agtcctcctg agccgcaacg gctctgaggt ctcggccagc ttcgacggct gggccaccgt   5160
ctcggtgatc gcgctctcca acatcctcca cgcctccgcc agcctcccgc ccgagtacca   5220
gaaccgcacg gaggggctcc tgggggtctg gaataacaat ccagaggacg acttcaggat   5280
gcccaatggc tccaccattc ccccagggag ccctgaggag atgcttttcc actttggaat   5340
gacctggcag atcaacggga caggcctcct tggcaagagg aatgaccagc tgccttccaa   5400
cttcacccct gttttctact cacaactgca aaaaaacagc tcctgggctg aacatttgat   5460
ctccaactgt gacggagata gctcatgcat ctatgacacc ctggccctgc gcaacgcaag   5520
catcggactt cacacgaggg aagtcagtaa aaactacgag caggcgaacg ccaccctcaa   5580
tcagtacccg ccctccatca atggtggtcg tgtgattgaa gcctacaagg ggcagaccac   5640
gctgattcag tacaccagca atgctgagga tgccaacttc acgctcagag acagctgcac   5700
cgacttggag ctctttgaga atgggacgtt gctgtggaca cccaagtcgc tggagccatt   5760
cactctggag attctagcaa gaagtgccaa gattggcttg gcatctgcac tccagcccag   5820
gactgtggtc tgccattgca atgcagagag ccagtgtttg tacaatcaga ccagcagggt   5880
gggcaactcc tccctggagg tggctggctg caagtgtgac gggggcacct tcggccgcta   5940
ctgcgagggc tccgaggatg cctgtgagga gccgtgcttc ccgagtgtcc actgcgttcc   6000
tgggaagggc tgcgaggcct gccctccaaa cctgactggg gatgggcggc actgtgcggc   6060
tctggggagc tctttcctgt gtcagaacca gtcctgccct gtgaattact gctacaatca   6120
```

```
aggccactgc tacatctccc agactctggg ctgtcagccc atgtgcacct gccccccagc   6180

cttcactgac agccgctgct tcctggctgg gaacaacttc agtccaactg tcaacctaga   6240

acttccctta agagtcatcc agctcttgct cagtgaagag gaaaatgcct ccatggcaga   6300

ggtcaacgcc tcggtggcat acagactggg gaccctggac atgcgggcct ttctccgcaa   6360

cagccaagtg gaacgaatcg attctgcagc accggcctcg ggaagcccca tccaacactg   6420

gatggtcatc tcggagttcc agtaccgccc tcggggcccg gtcattgact tcctgaacaa   6480

ccagctgctg gccgcggtgg tggaggcgtt cttataccac gttccacgga ggagtgagga   6540

gcccaggaac gacgtggtct tccagcccat ctccggggaa gacgtgcgcg atgtgacagc   6600

cctgaacgtg agcacgctga aggcttactt cagatgcgat ggctacaagg gctacgacct   6660

ggtctacagc ccccagagcg gcttcacctg cgtgtccccg tgcagtaggg gctactgtga   6720

ccatggaggc cagtgccagc acctgcccag tgggccccgc tgcagctgtg tgtccttctc   6780

catctacacg gcctggggcg agcactgtga gcacctgagc atgaaactcg acgcgttctt   6840

cggcatcttc tttggggccc tgggcggcct cttgctgctg gggtcggga cgttcgtggt   6900

cctgcgcttc tggggttgct ccggggccag gttctcctat ttcctgaact cagctgaggc   6960

cttgccttga aggggcagct gtggcctagg ctacctcaag actcacctca tccttaccgc   7020

acatttaagg cgccattgct tttgggagac tggaaaaggg aaggtgactg aaggctgtca   7080

ggattcttca aggagaatga atactgggaa tcaagacaag actataccttt atccataggc   7140

gcaggtgcac agggggaggc cataaagatc aaacatgcat ggatgggtcc tcacgcagac   7200

acacccacag aaggacacta gcctgtgcac gcgcgcgtgc acacacacac acacacacac   7260

gagttcataa tgtggtgatg gccctaagtt aagcaaaatg cttctgcaca caaaactctc   7320

tggtttactt caaattaact ctatttaaat aaagtctctc tgactttttg tgtctccaaa   7380

a                                                                   7381
```

<210> SEQ ID NO 30
<211> LENGTH: 14360
<212> TYPE: DNA
<213> ORGANISM: Homo sapiens

<400> SEQUENCE: 30

```
tttcgccagc tcctctgggg gtgacaggca agtgagacgt gctcagagct ccgatgccaa     60

ggccagggac catggcgctg tgtctgctga ccttggtcct ctcgctcttg cccccacaag    120

ctgctgcaga acaggacctc agtgtgaaca gggctgtgtg ggatggagga gggtgcatct    180

cccaagggga cgtcttgaac cgtcagtgcc agcagctgtc tcagcacgtt aggacaggtt    240

ctgcggcaaa caccgccaca ggtacaacat ctacaaatgt cgtggagcca agaatgtatt    300

tgagttgcag caccaaccct gagatgacct cgattgagtc cagtgtgact tcagacactc    360

ctggtgtctc cagtaccagg atgacaccaa cagaatccag aacaacttca gaatctacca    420

gtgacagcac cacacttttc cccagttcta ctgaagacac ttcatctcct acaactcctg    480

aaggcaccga cgtgcccatg tcaacaccaa gtgaagaaag catttcatca acaatggctt    540

ttgtcagcac tgcacctctt cccagttttg aggcctacac atctttaaca tataaggttg    600

atatgagcac acctctgacc acttctactc aggcaagttc atctcctact actcctgaaa    660

gcaccaccat acccaaatca actaacagtg aaggaagcac tccattaaca agtatgcctg    720

ccagcaccat gaaggtggcc agttcagagg ctatcaccct tttgacaact cctgttgaaa    780

tcagcacacc tgtgaccatt tctgctcaag ccagttcatc tcctacaact gctgaaggtc    840
```

-continued

```
ccagcctgtc aaactcagct cctagtggag gaagcactcc attaacaaga atgcctctca    900
gcgtgatgct ggtggtcagt tctgaggcta gcaccctttc aacaactcct gctgccacca    960
acattcctgt gatcacttct actgaagcca gttcatctcc tacaacggct gaaggcacca   1020
gcataccaac ctcaacttat actgaaggaa gcactccatt aacaagtacg cctgccagca   1080
ccatgccggt tgccacttct gaaatgagca cactttcaat aactcctgtt gacaccagca   1140
cacttgtgac cacttctact gaacccagtt cacttcctac aactgctgaa gctaccagca   1200
tgctaacctc aactcttagt gaaggaagca ctccattaac aaatatgcct gtcagcacca   1260
tattggtggc cagttctgag gctagcacca cttcaacaat tcctgttgac tccaaaactt   1320
ttgtgaccac tgctagtgaa gccagctcat ctcccacaac tgctgaagat accagcattg   1380
caacctcaac tcctagtgaa ggaagcactc cattaacaag tatgcctgtc agcaccactc   1440
cagtggccag ttctgaggct agcaaccttt caacaactcc tgttgactcc aaaactcagg   1500
tgaccacttc tactgaagcc agttcatctc ctccaactgc tgaagttaac agcatgccaa   1560
cctcaactcc tagtgaagga agcactccat taacaagtat gtctgtcagc accatgccgg   1620
tggccagttc tgaggctagc accctttcaa caactcctgt tgacaccagc acacctgtga   1680
ccacttctag tgaagccagt tcatcttcta caactcctga aggtaccagc ataccaacct   1740
caactcctag tgaaggaagc actccattaa caaacatgcc tgtcagcacc aggctggtgg   1800
tcagttctga ggctagcacc acttcaacaa ctcctgctga ctccaacact tttgtgacca   1860
cttctagtga agctagttca tcttctacaa ctgctgaagg taccagcatg ccaacctcaa   1920
cttacagtga aagaggcact acaataacaa gtatgtctgt cagcaccaca ctggtggcca   1980
gttctgaggc tagcaccctt tcaacaactc ctgttgactc caacactcct gtgaccactt   2040
caactgaagc cacttcatct tctacaactg cggaaggtac cagcatgcca acctcaactt   2100
atactgaagg aagcactcca ttaacaagta tgcctgtcaa caccacactg gtggccagtt   2160
ctgaggctag caccctttca acaactcctg ttgacaccag cacacctgtg accacttcaa   2220
ctgaagccag ttcctctcct acaactgctg atggtgccag tatgccaacc tcaactccta   2280
gtgaaggaag cactccatta acaagtatgc ctgtcagcaa aacgctgttg accagttctg   2340
aggctagcac cctttcaaca actcctcttg acacaagcac acatatcacc acttctactg   2400
aagccagttg ctctcctaca accactgaag gtaccagcat gccaatctca actcctagtg   2460
aaggaagtcc tttattaaca agtatacctg tcagcatcac accggtgacc agtcctgagg   2520
ctagcaccct ttcaacaact cctgttgact ccaacagtcc tgtgaccact tctactgaag   2580
tcagttcatc tcctacacct gctgaaggta ccagcatgcc aacctcaact tatagtgaag   2640
gaagaactcc tttaacaagt atgcctgtca gcaccacact ggtggccact tctgcaatca   2700
gcaccctttc aacaactcct gttgacacca gcacacctgt gaccaattct actgaagccc   2760
gttcgtctcc tacaacttct gaaggtacca gcatgccaac ctcaactcct ggggaaggaa   2820
gcactccatt aacaagtatg cctgacagca ccacgccggt agtcagttct gaggctagaa   2880
cactttcagc aactcctgtt gacaccagca cacctgtgac cacttctact gaagccactt   2940
catctcctac aactgctgaa ggtaccagca taccaacctc gactcctagt gaaggaacga   3000
ctccattaac aagcacacct gtcagccaca cgctggtggc caattctgag gctagcaccc   3060
tttcaacaac tcctgttgac tccaacactc ctttgaccac ttctactgaa gccagttcac   3120
ctcctcccac tgctgaaggt accagcatgc caacctcaac tcctagtgaa ggaagcactc   3180
cattaacacg tatgcctgtc agcaccacaa tggtggccag ttctgaaacg agcacacttt   3240
```

-continued

```
caacaactcc tgctgacacc agcacacctg tgaccactta ttctcaagcc agttcatctt   3300
ctacaactgc tgacggtacc agcatgccaa cctcaactta tagtgaagga agcactccac   3360
taacaagtgt gcctgtcagc accaggctgg tggtcagttc tgaggctagc accctttcca   3420
caactcctgt cgacaccagc atacctgtca ccacttctac tgaagccagt tcatctccta   3480
caactgctga aggtaccagc ataccaacct cacctcccag tgaaggaacc actccgttag   3540
caagtatgcc tgtcagcacc acgctggtgg tcagttctga ggctaacacc ctttcaacaa   3600
ctcctgtgga ctccaaaact caggtggcca cttctactga agccagttca cctcctccaa   3660
ctgctgaagt taccagcatg ccaacctcaa ctcctggaga aagaagcact ccattaacaa   3720
gtatgcctgt cagacacacg ccagtggcca gttctgaggc tagcaccctt tcaacatctc   3780
ccgttgacac cagcacacct gtgaccactt ctgctgaaac cagttcctct cctacaaccg   3840
ctgaaggtac cagcttgcca acctcaacta ctagtgaagg aagtactcta ttaacaagta   3900
tacctgtcag caccacgctg gtgaccagtc ctgaggctag caccctttta acaactcctg   3960
ttgacactaa aggtcctgtg gtcacttcta atgaagtcag ttcatctcct acacctgctg   4020
aaggtaccag catgccaacc tcaacttata gtgaaggaag aactccttta acaagtatac   4080
ctgtcaacac cacactggtg gccagttctg caatcagcat cctttcaaca actcctgttg   4140
acaacagcac acctgtgacc acttctactg aagcctgttc atctcctaca acttctgaag   4200
gtaccagcat gccaaactca aatcctagtg aaggaaccac tccgttaaca agtatacctg   4260
tcagcaccac gccggtagtc agttctgagg ctagcaccct ttcagcaact cctgttgaca   4320
ccagcacccc tgggaccact tctgctgaag ccacttcatc tcctacaact gctgaaggta   4380
tcagcatacc aacctcaact cctagtgaag gaaagactcc attaaaaagt atacctgtca   4440
gcaacacgcc ggtggccaat tctgaggcta gcaccctttc aacaactcct gttgactcta   4500
acagtcctgt ggtcacttct acagcagtca gttcatctcc tacacctgct gaaggtacca   4560
gcatagcaat ctcaacgcct agtgaaggaa gcactgcatt aacaagtata cctgtcagca   4620
ccacaacagt ggccagttct gaaatcaaca gcctttcaac aactcctgct gtcaccagca   4680
cacctgtgac cacttattct caagccagtt catctcctac aactgctgac ggtaccagca   4740
tgcaaacctc aacttatagt gaaggaagca ctccactaac aagtttgcct gtcagcacca   4800
tgctggtggt cagttctgag gctaacaccc tttcaacaac ccctattgac tccaaaactc   4860
aggtgaccgc ttctactgaa gccagttcat ctacaaccgc tgaaggtagc agcatgacaa   4920
tctcaactcc tagtgaagga agtcctctat taacaagtat acctgtcagc accacgccgg   4980
tggccagtcc tgaggctagc accctttcaa caactcctgt tgactccaac agtcctgtga   5040
tcacttctac tgaagtcagt tcatctccta cacctgctga aggtaccagc atgccaacct   5100
caacttatac tgaaggaaga actcctttaa caagtataac tgtcagaaca acaccggtgg   5160
ccagctctgc aatcagcacc ctttcaacaa ctcccgttga caacagcaca cctgtgacca   5220
cttctactga agcccgttca tctcctacaa cttctgaagg taccagcatg ccaaactcaa   5280
ctcctagtga aggaaccact ccattaacaa gtatacctgt cagcaccacg ccggtactca   5340
gttctgaggc tagcaccctt tcagcaactc ctattgacac cagcacccct gtgaccactt   5400
ctactgaagc cacttcgtct cctacaactg ctgaaggtac cagcatacca acctcgactc   5460
ttagtgaagg aatgactcca ttaacaagca cacctgtcag ccacacgctg gtggccaatt   5520
ctgaggctag caccctttca acaactcctg ttgactctaa cagtcctgtg gtcacttcta   5580
cagcagtcag ttcatctcct acacctgctg aaggtaccag catagcaacc tcaacgccta   5640
```

```
gtgaaggaag cactgcatta acaagtatac ctgtcagcac cacaacagtg gccagttctg   5700
aaaccaacac cctttcaaca actcccgctg tcaccagcac acctgtgacc acttatgctc   5760
aagtcagttc atctcctaca actgctgacg gtagcagcat gccaacctca actcctaggg   5820
aaggaaggcc tccattaaca agtatacctg tcagcaccac aacagtggcc agttctgaaa   5880
tcaacaccct ttcaacaact cttgctgaca ccaggacacc tgtgaccact tattctcaag   5940
ccagttcatc tcctacaact gctgatggta ccagcatgcc aaccccagct tatagtgaag   6000
gaagcactcc actaacaagt atgcctctca gcaccacgct ggtggtcagt tctgaggcta   6060
gcactctttc cacaactcct gttgacacca gcactcctgc caccacttct actgaaggca   6120
gttcatctcc tacaactgca ggaggtacca gcatacaaac ctcaactcct agtgaacgga   6180
ccactccatt agcaggtatg cctgtcagca ctacgcttgt ggtcagttct gagggtaaca   6240
ccctttcaac aactcctgtt gactccaaaa ctcaggtgac caattctact gaagccagtt   6300
catctgcaac cgctgaaggt agcagcatga caatctcagc tcctagtgaa ggaagtcctc   6360
tactaacaag tatacctctc agcaccacgc cggtggccag tcctgaggct agcacccttt   6420
caacaactcc tgttgactcc aacagtcctg tgatcacttc tactgaagtc agttcatctc   6480
ctatacctac tgaaggtacc agcatgcaaa cctcaactta tagtgacaga agaactcctt   6540
taacaagtat gcctgtcagc accacagtgg tggccagttc tgcaatcagc accctttcaa   6600
caactcctgt tgacaccagc acacctgtga ccaattctac tgaagcccgt tcatctccta   6660
caacttctga aggtaccagc atgccaacct caactcctag tgaaggaagc actccattca   6720
caagtatgcc tgtcagcacc atgccggtag ttacttctga ggctagcacc ctttcagcaa   6780
ctcctgttga caccagcaca cctgtgacca cttctactga agccacttca tctcctacaa   6840
ctgctgaagg taccagcata ccaacttcaa ctcttagtga aggaacgact ccattaacaa   6900
gtatacctgt cagccacacg ctggtggcca attctgaggt tagcaccctt tcaacaactc   6960
ctgttgactc caacactcct ttcactactt ctactgaagc cagttcacct cctcccactg   7020
ctgaaggtac cagcatgcca acctcaactt ctagtgaagg aaacactcca ttaacacgta   7080
tgcctgtcag caccacaatg gtggccagtt ttgaaacaag cacactttct acaactcctg   7140
ctgacaccag cacacctgtg actacttatt ctcaagccgg ttcatctcct acaactgctg   7200
acgatactag catgccaacc tcaacttata gtgaaggaag cactccacta acaagtgtgc   7260
ctgtcagcac catgccggtg gtcagttctg aggctagcac ccattccaca actcctgttg   7320
acaccagcac acctgtcacc acttctactg aagccagttc atctcctaca actgctgaag   7380
gtaccagcat accaacctca cctcctagtg aaggaaccac tccgttagca agtatgcctg   7440
tcagcaccac gccggtggtc agttctgagg ctggcaccct ttccacaact cctgttgaca   7500
ccagcacacc tatgaccact tctactgaag ccagttcatc tcctacaact gctgaagata   7560
tcgtcgtgcc aatctcaact gctagtgaag gaagtactct attaacaagt atacctgtca   7620
gcaccacgcc agtggccagt cctgaggcta gcaccctttc aacaactcct gttgactcca   7680
acagtcctgt ggtcacttct actgaaatca gttcatctgc tacatccgct gaaggtacca   7740
gcatgcctac ctcaacttat agtgaaggaa gcactccatt aagaagtatg cctgtcagca   7800
ccaagccgtt ggccagttct gaggctagca ctctttcaac aactcctgtt gacaccagca   7860
tacctgtcac cacttctact gaaaccagtt catctcctac aactgcaaaa gataccagca   7920
tgccaatctc aactcctagt gaagtaagta cttcattaac aagtatactt gtcagcacca   7980
tgccagtggc cagttctgag gctagcaccc tttcaacaac tcctgttgac accaggacac   8040
```

```
ttgtgaccac ttccactgga accagttcat ctcctacaac tgctgaaggt agcagcatgc   8100

caacctcaac tcctggtgaa agaagcactc cattaacaaa tatacttgtc agcaccacgc   8160

tgttggccaa ttctgaggct agcacccttt caacaactcc tgttgacacc agcacacctg   8220

tcaccacttc tgctgaagcc agttcttctc ctacaactgc tgaaggtacc agcatgcgaa   8280

tctcaactcc tagtgatgga agtactccat taacaagtat acttgtcagc accctgccag   8340

tggccagttc tgaggctagc accgtttcaa caactgctgt tgacaccagc atacctgtca   8400

ccacttctac tgaagccagt tcctctccta caactgctga agttaccagc atgccaacct   8460

caactcctag tgaaacaagt actccattaa ctagtatgcc tgtcaaccac acgccagtgg   8520

ccagttctga ggctggcacc ctttcaacaa ctcctgttga caccagcaca cctgtgacca   8580

cttctactaa agccagttca tctcctacaa ctgctgaagg tatcgtcgtg ccaatctcaa   8640

ctgctagtga aggaagtact ctattaacaa gtatacctgt cagcaccacg ccggtggcca   8700

gttctgaggc tagcaccctt tcaacaactc ctgttgatac cagcatacct gtcaccactt   8760

ctactgaagg cagttcttct cctacaactg ctgaaggtac cagcatgcca atctcaactc   8820

ctagtgaagt aagtactcca ttaacaagta tacttgtcag caccgtgcca gtggccggtt   8880

ctgaggctag caccctttca acaactcctg ttgacaccag gacacctgtc accacttctg   8940

ctgaagctag ttcttctcct acaactgctg aaggtaccag catgccaatc tcaactcctg   9000

gcgaaagaag aactccatta acaagtatgt ctgtcagcac catgccggtg gccagttctg   9060

aggctagcac cctttcaaga actcctgctg acaccagcac acctgtgacc acttctactg   9120

aagccagttc ctctcctaca actgctgaag gtaccggcat accaatctca actcctagtg   9180

aaggaagtac tccattaaca agtatacctg tcagcaccac gccagtggcc attcctgagg   9240

ctagcaccct ttcaacaact cctgttgact ccaacagtcc tgtggtcact tctactgaag   9300

tcagttcatc tcctacacct gctgaaggta ccagcatgcc aatctcaact tatagtgaag   9360

gaagcactcc attaacaggt gtgcctgtca gcaccacacc ggtgaccagt tctgcaatca   9420

gcaccctttc aacaactcct gttgacacca gcacacctgt gaccacttct actgaagccc   9480

attcatctcc tacaacttct gaaggtacca gcatgccaac ctcaactcct agtgaaggaa   9540

gtactccatt aacatatatg cctgtcagca ccatgctggt agtcagttct gaggatagca   9600

ccctttcagc aactcctgtt gacaccagca cacctgtgac cacttctact gaagccactt   9660

catctacaac tgctgaaggt accagcattc caacctcaac tcctagtgaa ggaatgactc   9720

cattaactag tgtacctgtc agcaacacgc cggtggccag ttctgaggct agcatccttt   9780

caacaactcc tgttgactcc aacactcctt tgaccacttc tactgaagcc agttcatctc   9840

ctcccactgc tgaaggtacc agcatgccaa cctcaactcc tagtgaagga agcactccat   9900

taacaagtat gcctgtcagc accacaacgg tggccagttc tgaaacgagc accctttcaa   9960

caactcctgc tgacaccagc acacctgtga ccacttattc tcaagccagt tcatctcctc  10020

caattgctga cggtactagc atgccaacct caacttatag tgaaggaagc actccactaa  10080

caaatatgtc tttcagcacc acgccagtgg tcagttctga ggctagcacc ctttccacaa  10140

ctcctgttga caccagcaca cctgtcacca cttctactga agccagttta tctcctacaa  10200

ctgctgaagg taccagcata ccaacctcaa gtcctagtga aggaaccact ccattagcaa  10260

gtatgcctgt cagcaccacg ccggtggtca gttctgaggt taacaccctt tcaacaactc  10320

ctgtggactc caacactctg gtgaccactt ctactgaagc cagttcatct cctacaatcg  10380

ctgaaggtac cagcttgcca acctcaacta ctagtgaagg aagcactcca ttatcaatta  10440
```

-continued

```
tgcctctcag taccacgccg gtggccagtt ctgaggctag caccctttca acaactcctg  10500
ttgacaccag cacacctgtg accacttctt ctccaaccaa ttcatctcct acaactgctg  10560
aagttaccag catgccaaca tcaactgctg gtgaaggaag cactccatta acaaatatgc  10620
ctgtcagcac cacaccggtg gccagttctg aggctagcac cctttcaaca actcctgttg  10680
actccaacac ttttgttacc agttctagtc aagccagttc atctccagca actcttcagg  10740
tcaccactat gcgtatgtct actccaagtg aaggaagctc ttcattaaca actatgctcc  10800
tcagcagcac atatgtgacc agttctgagg ctagcacacc ttccactcct tctgttgaca  10860
gaagcacacc tgtgaccact tctactcaga gcaattctac tcctacacct cctgaagtta  10920
tcaccctgcc aatgtcaact cctagtgaag taagcactcc attaaccatt atgcctgtca  10980
gcaccacatc ggtgaccatt tctgaggctg gcacagcttc aacacttcct gttgacacca  11040
gcacacctgt gatcacttct acccaagtca gttcatctcc tgtgactcct gaaggtacca  11100
ccatgccaat ctggacgcct agtgaaggaa gcactccatt aacaactatg cctgtcagca  11160
ccacacgtgt gaccagctct gagggtagca ccctttcaac accttctgtt gtcaccagca  11220
cacctgtgac cacttctact gaagccattt catcttctgc aactcttgac agcaccacca  11280
tgtctgtgtc aatgcccatg gaaataagca cccttgggac cactattctt gtcagtacca  11340
cacctgttac gaggtttcct gagagtagca ccccttccat accatctgtt tacaccagca  11400
tgtctatgac cactgcctct gaaggcagtt catctcctac aactcttgaa ggcaccacca  11460
ccatgcctat gtcaactacg agtgaaagaa gcactttatt gacaactgtc ctcatcagcc  11520
ctatatctgt gatgagtcct tctgaggcca gcacactttc aacacctcct ggtgatacca  11580
gcacaccttt gctcacctct accaaagccg gttcattctc catacctgct gaagtcacta  11640
ccatacgtat ttcaattacc agtgaaagaa gcactccatt aacaactctc cttgtcagca  11700
ccacacttcc aactagcttt cctggggcca gcatagcttc gacacctcct cttgacacaa  11760
gcacaacttt tacccttct actgacactg cctcaactcc cacaattcct gtagccacca  11820
ccatatctgt atcagtgatc acagaaggaa gcacacctgg gacaaccatt tttattccca  11880
gcactcctgt caccagttct actgctgatg tctttcctgc aacaactggt gctgtatcta  11940
cccctgtgat aacttccact gaactaaaca caccatcaac ctccagtagt agtaccacca  12000
catctttttc aactactaag gaatttacaa cacccgcaat gactactgca gctcccctca  12060
catatgtgac catgtctact gcccccagca cacccagaac aaccagcaga ggctgcacta  12120
cttctgcatc aacgctttct gcaaccagta cacctcacac ctctacttct gtcaccaccc  12180
gtcctgtgac cccttcatca gaatccagca ggccgtcaac aattacttct cacaccatcc  12240
cacctacatt tcctcctgct cactccagta cacctccaac aacctctgcc tcctccacga  12300
ctgtgaaccc tgaggctgtc accaccatga ccaccaggac aaaacccagc acacggacca  12360
cttccttccc cacggtgacc accaccgctg tccccacgaa tactacaatt aagagcaacc  12420
ccacctcaac tcctactgtg ccaagaacca caacatgctt tggagatggg tgccagaata  12480
cggcctctcg ctgcaagaat ggaggcacct gggatgggct caagtgccag tgtcccaacc  12540
tctattatgg ggagttgtgt gaggaggtgg tcagcagcat tgacataggg ccaccggaga  12600
ctatctctgc ccaaatggaa ctgactgtga cagtgaccag tgtgaagttc accgaagagc  12660
taaaaaacca ctcttcccag gaattccagg agttcaaaca gacattcacg gaacagatga  12720
atattgtgta ttccgggatc cctgagtatg tcggggtgaa catcacaaag ctacgtcttg  12780
gcagtgtggt ggtggagcat gacgtcctcc taagaaccaa gtacacacca gaatacaaga  12840
```

-continued

```
cagtattgga caatgccacc gaagtagtga aagagaaaat cacaaaagtg accacacagc  12900

aaataatgat taatgatatt tgctcagaca tgatgtgttt caacaccact ggcacccaag  12960

tgcaaaacat tacggtgacc cagtacgacc ctgaagagga ctgccggaag atggccaagg  13020

aatatggaga ctacttcgta gtggagtacc gggaccagaa gccatactgc atcagcccct  13080

gtgagcctgg cttcagtgtc tccaagaact gtaacctcgg caagtgccag atgtctctaa  13140

gtggacctca gtgcctctgc gtgaccacgg aaactcactg gtacagtggg gagacctgta  13200

accagggcac ccagaagagt ctggtgtacg gcctcgtggg ggcaggggtc gtgctgatgc  13260

tgatcatcct ggtagctctc ctgatgctcg ttttccgctc caagagagag gtgaaacggc  13320

aaaagtacag attgtctcag ttatacaagt ggcaagaaga ggacagtgga ccagctcctg  13380

ggaccttcca aaacattggc tttgacatct gccaagatga tgattccatc cacctggagt  13440

ccatctatag taatttccag ccctccttga gacacataga ccctgaaaca aagatccgaa  13500

ttcagaggcc tcaggtaatg acgacatcat tttaaggcat ggagctgaga agtctgggag  13560

tgaggagatc ccagtccggc taagcttggt ggagcatttt cccattgaga gccttccatg  13620

ggaactcaat gttcccattg taagtacagg aaacaagccc tgtacttacc aaggagaaag  13680

aggagagaca gcagtgctgg gagattctca aatagaaacc cgtggacgct ccaatgggct  13740

tgtcatgata tcaggctagg ctttcctgct catttttcaa agacgctcca gatttgaggg  13800

tactctgact gcaacatctt tcaccccatt gatcgccagg attgatttgg ttgatctggc  13860

tgagcaggcg ggtgtccccg tcctccctca ctgccccata tgtgtccctc ctaaagctgc  13920

atgctcagtt gaagaggacg agaggacgac cttctctgat agaggaggac cacgcttcag  13980

tcaaaggcat acaagtatct atctggactt ccctgctagc acttccaaac aagctcagag  14040

atgttcctcc cctcatctgc ccgggttcag taccatggac agcgccctcg acccgctgtt  14100

tacaaccatg accccttgga cactggactg catgcacttt acatatcaca aaatgctctc  14160

ataagaatta ttgcatacca tcttcatgaa aaacacctgt atttaaatat agagcattta  14220

ccttttggta tataagattg tgggtatttt ttaagttctt attgttatga gttctgattt  14280

tttccttagt aaatattata atatatattt gtagtaacta aaaataataa agcaatttta  14340

ttacaatttt aaaaaaaaaa                                              14360
```

METHOD FOR JUDGING LYMPH NODE METASTASIS OF STOMACH CANCER AND KIT USED THEREFOR

FIELD OF THE INVENTION

The present invention relates to a marker for judging lymph node metastasis of stomach cancer, primers for amplifying cDNA derived from the marker, and a method of judging lymph node metastasis of stomach cancer using the marker.

BACKGROUND

In diagnosis of stomach cancer, detection of cancer cells in lymph nodes (diagnosis of lymph node metastasis) becomes information useful for determining operation range or for determining postoperative chemotherapy. At present, diagnosis of lymph node metastasis is carried out by a medical pathologist by tissue diagnosis with a frozen section or paraffin section of lymph node tissue (for example, HE (hematoxylin-eosin) staining method, IHC (immunohistochemical method), etc.). However, even if cancer cells are present in lymph nodes, the cancer cells will be overlooked if a section is prepared from a cancer cell-free cut surface and the section is subjected to tissue diagnosis. In addition, diagnosis results may vary depending on the level of skill of a medical pathologist who makes the diagnosis.

Under these circumstances, studies on molecular diagnosis of cancer by LAMP (loop-mediated isothermal amplification method) and PCR (polymerase chain reaction) have been extensively conducted. Molecular diagnosis can be carried out by detection of molecular markers (for example, a protein expressed specifically in a cancer cell, a gene encoding the protein or an mRNA of the gene).

A wide variety of proteins have been expressed in stomach cancer cells, and molecules capable of serving as stomach cancer markers have been extensively searched.

For example, JP-A 2006-223303 describes that the expression levels of genes for TFF1, TFF2, FABP1, CK20, MUC2, CEA, TACSTD1, MASPIN, PRSS4, GW112 and ACTB are examined in KATOIII cells, a cell line derived from human stomach cancer, or in cells in an intraperitoneal irrigation solution collected from a stomach cancer patient, and that reappearance of stomach cancer is predicted on the basis of the expression levels of these genes.

JP-A 2006-526998 describes a method of diagnosing stomach cancer by measuring the expression levels of genes for EEFA1A, TUBA6, FKBP1A, PKM2, LDHA, RPL4, ARF1, SURF4, KRT8, GAPD, HSPCB, PGK1, HMGIY, K-ALPHA-1, FTH1, HSPA8, SH3GLB2, ACTB, HSPCA, TMSB4X, PYCR1, ATF4, JUN, HSPB1, IGKC, SNC73, CD74, LOC131177 (FAM3D), AGR2, and IMAGE:4296901 (pepsin A). It also describes a method of diagnosing metastatic stomach cancer by measuring the expression levels of genes for GADD45B, JUN, HMGIY, GSTP1, LMNA, ESRRA, PLK, CD44, IGFBP3, PKM2, FKBP1A, KRT8, TMSB4X, GAPD, ATP5A1, PTMA, CALM2 and NET1.

JP-A 2005-304497 describes that stomach cancer can be diagnosed on the basis of the expression levels of genes for PVT1, MYC, FOLR1, PLUNC (LUNX), E2F1, TGIF2, TNFRSF5, NCOA3, ELMO2, MYBL2, NCOA3 (AIB1), PTPN1, PRex1, BCAS1, ZNF217, STK6 (BTAK), CUL4B, MCF2, CTAG, SDC1, DNMT3A, MLH1, CTNNB1, CCK, ZNF131, CDK6, MET, MYC, PVT1, EGR2, KSAM (FGFR2), PKY (HIPK3), LMO2, CD44, KRAS, KRAG (SSPN), CYP1A1, IQGAP1, FURIN (PACE), PPARBP, ERBB2, CCNE1, MYBL2, BAIAP1, PTPRG, N33, TEK, MTAP, CDKN2A (p16), MLLT3, JAK2, GASC1, D9S913, SMAD4, MADH2, MADH7 (SMAD7), DCC, MALT1, GRP, BCL2, FVT1, SERPINB (PI5) and CTDP1.

However, the expression levels of the above genes in lymph node cells recognized to have metastasis of stomach cancer-derived cancer cells and in normal lymph node cells were not confirmed in any of the above patent literatures. Accordingly, it is not clear which of the genes enumerated in the literatures supra are useful as markers for judging lymph node metastasis of stomach cancer.

As molecular markers for judging lymph node metastasis of stomach cancer (also referred to hereinafter as simply "markers"), human carcinoembryonic antigen (CEA) and cytokeratin 20 (CK20) have been reported (Keisuke Kubota et. al., "Quantitative detection of micrometastases in the lymph nodes of gastric cancer patients with real-time RT-PCR: a comparative study with immunohistochemistry", International Journal of Cancer, May 2003, Vol. 105, pages 136-143).

SUMMARY

A first aspect of the invention is A method for judging the lymph node metastasis of stomach cancer, comprising steps of:

preparing a detection sample from lymph nodes collected from the living body, measuring the amount of at least one marker for detecting lymph node metastasis of stomach cancer, said marker being contained in the detection sample and comprising an mRNA, or a fragment thereof, of a gene coding for at least one protein selected from the group consisting of trefoll factor 1, anterior gradient 2 homolog, serine protease 8, mucin 1, mucin 4, and mucin 17, and judging the presence of lymph nodes metastasis of stomach cancer when the marker is judged to occur in excess.

A second aspect of the invention is A method for judging the lymph node metastasis of stomach cancer, comprising steps of:

preparing a detection sample from lymph nodes collected from the living body, measuring the amount of at least one marker for detecting lymph node metastasis of stomach cancer by using a primer set for detecting the marker, and judging the presence of lymph nodes metastasis of stomach cancer when the marker occurs in excess, said marker being contained in the detection sample and comprising an mRNA, or a fragment thereof, of a gene coding for at least one protein selected from the group consisting of trefoil factor 1, anterior gradient 2 homolog, serine protease 8, mucin 1, mucin 4, and mucin 17, and said primer set being at least one primer set selected from the group consisting of:

(1) a primer set for detection of trefoil factor 1, comprising a first primer selected from the group consisting of:

(a) a polynucleotide having a sequence set forth in SEQ ID NO 1, and (b) a polynucleotide having a mutated nucleotide sequence of the polynucleotide (a) with substitution, deletion, insertion or addition of at least one nucleotide and having a primer function in a nucleic acid amplification reaction, and a second primer selected from the group consisting of:

(c) a polynucleotide having a sequence set forth in SEQ ID NO 2, and (d) a polynucleotide having a mutated nucleotide sequence of the polynucleotide (c) with substitution, deletion, insertion or addition of at least one nucleotide and having a primer function in a nucleic acid amplification reaction;

(2) a primer set for detection of anterior gradient 2 homolog, comprising a third primer selected from the group consisting of:

(e) a polynucleotide having a sequence set forth in SEQ ID NO 3, and (f) a polynucleotide having a mutated nucleotide sequence of the polynucleotide (e) with substitution, deletion, insertion or addition of at least one nucleotide and having a primer function in a nucleic acid amplification reaction, and a fourth primer selected from the group consisting of:

(g) a polynucleotide having a sequence set forth in SEQ ID NO 4, and (h) a polynucleotide having a mutated nucleotide sequence of the polynucleotide (g) with substitution, deletion, insertion or addition of at least one nucleotide and having a primer function in a nucleic acid amplification reaction;

(3) a primer set for detection of serine protease 8, comprising a fifth primer selected from the group consisting of:

(i) a polynucleotide having a sequence set forth in SEQ ID NO 5, and (j) a polynucleotide having a mutated nucleotide sequence of the polynucleotide (i) with substitution, deletion, insertion or addition of at least one nucleotide and having a primer function in a nucleic acid amplification reaction, and a sixth primer selected from the group consisting of:

(k) a polynucleotide having a sequence set forth in SEQ ID NO 6, and (l) a polynucleotide having a mutated nucleotide sequence of the polynucleotide (k) with substitution, deletion, insertion or addition of at least one nucleotide and having a primer function in a nucleic acid amplification reaction, (4) a primer set for detection of mucin 1, comprising a seventh primer selected from the group consisting of:

(m) a polynucleotide having a sequence set forth in SEQ ID NO 7, and (n) a polynucleotide having a mutated nucleotide sequence of the polynucleotide (m) with substitution, deletion, insertion or addition of at least one nucleotide and having a primer function in a nucleic acid amplification reaction, and an eighth primer selected from the group consisting of:

(o) a polynucleotide having a sequence set forth in SEQ ID NO 8, and (p) a polynucleotide having a mutated nucleotide sequence of the polynucleotide (o) with substitution, deletion, insertion or addition of at least one nucleotide and having a primer function in a nucleic acid amplification reaction, (5) a primer set for detection of mucin 4, comprising a ninth primer selected from the group consisting of:

(q) a polynucleotide having a sequence set forth in SEQ ID NO 9, and (r) a polynucleotide having a mutated nucleotide sequence of the polynucleotide (q) with substitution, deletion, insertion or addition of at least one nucleotide and having a primer function in a nucleic acid amplification reaction, and a tenth primer selected from the group consisting of:

(s) a polynucleotide having a sequence set forth in SEQ ID NO 10, and (t) a polynucleotide having a mutated nucleotide sequence of the polynucleotide (s) with substitution, deletion, insertion or addition of at least one nucleotide and having a primer function in a nucleic acid amplification reaction; and (6) a primer set for detection of mucin 17, comprising an eleventh primer selected from the group consisting of:

(u) a polynucleotide having a sequence set forth in SEQ ID NO 11, and (v) a polynucleotide having a mutated nucleotide sequence of the polynucleotide (u) with substitution, deletion, insertion or addition of at least one nucleotide and having a primer function in a nucleic acid amplification reaction, and a twelfth primer selected from the group consisting of:

(w) a polynucleotide having a sequence set forth in SEQ ID NO 12, and (x) a polynucleotide having a mutated nucleotide sequence of the polynucleotide (w) with substitution, deletion, insertion or addition of at least one nucleotide and having a primer function in a nucleic acid amplification reaction.

A third aspect of the invention is a reagent kit for detecting the lymph node metastasis of stomach cancer, which comprises:

primers for detecting an mRNA, or a fragment thereof, of a gene encoding at least one protein selected from the group consisting of trefoil factor 1, anterior gradient 2 homolog, serine protease 8, mucin 1, mucin 4 and mucin 17, and a lysis solution for lysing an mRNA in a lymph node cell, wherein the primers is used for detecting lymph node metastasis marker of stomach cancer

DETAILED DESCRIPTION OF THE PREFERRED EMBODIMENTS

Figure 1:
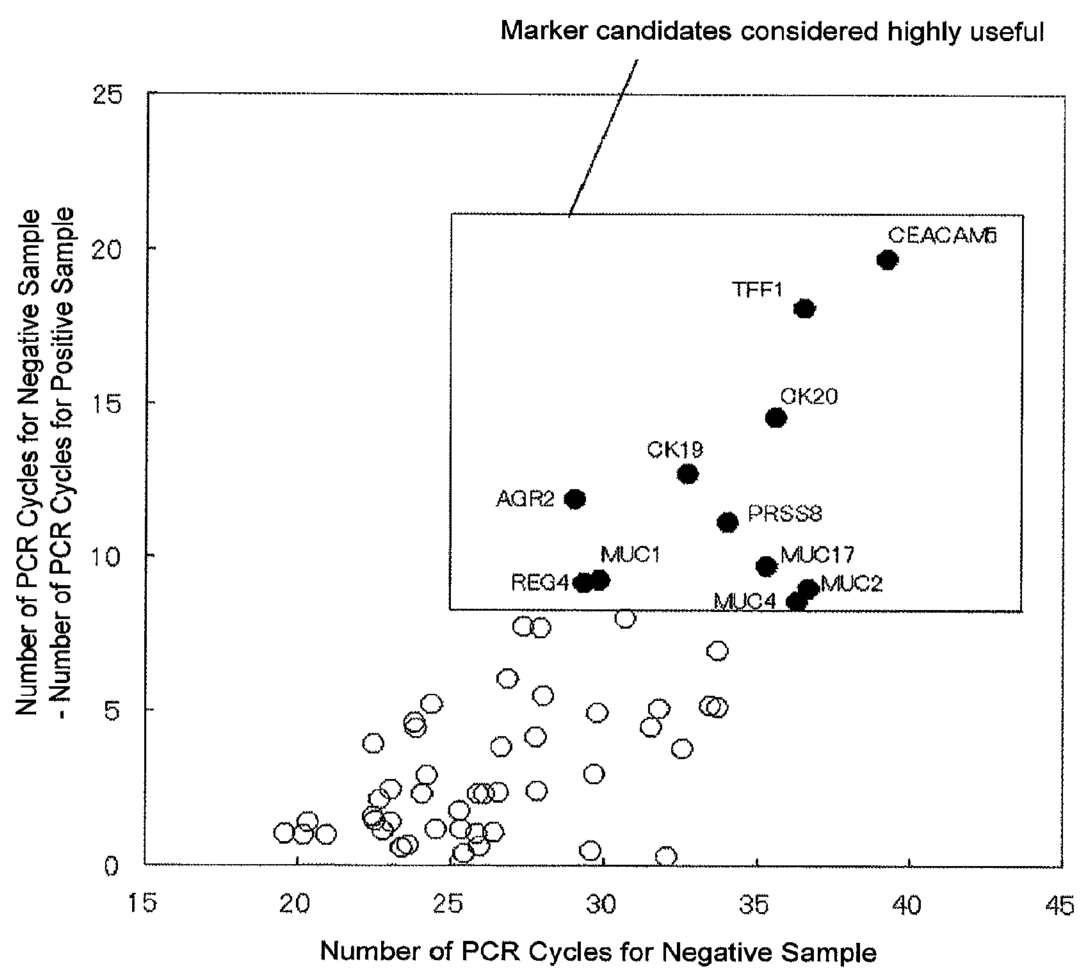
FIG. 1 is a graph showing the results in Table 1.

The preferred embodiments of the present invention are described hereinafter with reference to the drawings.

The marker in an embodiment of the present invention is either an mRNA of a gene encoding a protein occurring in excess in a cancer cell derived from stomach cancer or a part of the mRNA. By detecting this marker, cancer cells in lymph nodes can be detected. In this specification, the phrase "occurring in excess" means occurrence in a larger amount than in normal cells in lymph nodes. The term "detecting" includes not only judgment of the presence or absence but also quantification. The "mRNA" includes not only a mature mRNA but also an mRNA precursor (for example, an mRNA before posttranscriptional splicing or polyadenylation modification).

A wide variety of proteins have been expressed in a stomach cancer cell. Even when it is found that a certain protein is contained in a large amount in a cancer cell, it cannot be judged whether or not the protein is useful as a marker of lymph node metastasis of stomach cancer. A useful marker of lymph node metastasis of stomach cancer is either an mRNA, or apart thereof, which encodes a protein which, among a wide variety of proteins expressed in cancer cells, is confirmed to occur in excess in cells of lymph nodes with transferred stomach cancer, rather than in cells of normal lymph nodes.

To detect the marker, a detection sample is preferably prepared. In an embodiment of the present invention, the detection sample is a sample prepared by lysing lymph node cells collected from the living body. The sample containing lymph node cells includes, for example, a sample of surgically excised cells containing lymph node cells, or a sample containing lymph node cells collected for biopsy, etc.

The detection sample can be prepared for example in the following manner. First, a lysing reagent (referred to hereinafter as "lysis solution") is added to lymph node cells followed by chemical and/or physical treatment thereby transferring (lysing) an mRNA contained in the cells into the liquid phase. The resulting mRNA-containing solution can be used as a detection sample.

The lysis solution in an embodiment of the present invention includes, for example, a buffer solution or the like and is not particularly limited insofar as it can lyse mRNA in lymph node cells. The buffer solution is preferably acidic to suppress RNA decomposition, which is specifically preferably in the range of pH 2.5 to 5.0, more preferably pH 3.0 to 4.0. To keep the pH in this range, known buffers such as glycine-HCl buffer and the like can be used. The concentration of the buffer is not particularly limited insofar as the pH of the buffer solution can be kept in the above-mentioned range.

Preferably a surfactant is contained in the lysis solution. The cell membrane and nuclear membrane are damaged by the surfactant, and due to this damage, nucleic acids in cells move easily to the solution. Insofar as the surfactant has such action, the surfactant is not particularly limited. The surfactant is preferably a nonionic surfactant, more preferably a polyoxyethylene-based nonionic surfactant.

The surfactant is particularly preferably a polyoxyethylene-based nonionic surfactant represented by the following formula:

$$R1—R2—(CH_2CH_2O)_n—H$$

wherein R1 represents a C10 to C22 alkyl group, alkenyl group, alkynyl group or isooctyl group: R2 represents —O— or —$(C_6H_4)$—O—; and n is an integer of 8 to 120. Examples include polyoxyethylene lauryl ether, polyoxyethylene cetyl ether, polyoxyethylene oleyl ether, polyoxyethylene myristyl ether, polyoxyethylene stearyl ether, polyoxyethylene nonyl phenyl ether, and polyoxyethylene isooctyl phenyl ether. Specifically, Brij 35 (polyoxyethylene (35) lauryl ether) or the like is preferable. The concentration of the surfactant in the lysis solution is preferably 0.1 to 6% (v/v), more preferably 1 to 5% (v/v).

When quantification of mRNA is performed by a nucleic acid amplification method described later, dimethyl sulfoxide (DMSO) is preferably contained in the lysis solution. Although a substance (inhibitor) inhibiting an enzyme reaction in nucleic acid amplification sometimes contained in lymph nodes, the influence of this inhibitor can be effectively reduced by the action of DMSO. DMSO also has an effect of inhibiting reduction in the activity of a nucleic-acid amplification enzyme. The concentration of DMSO in the lysis solution is preferably 1 to 50% (v/v), more preferably 5 to 30% (v/v), most preferably 10 to 25% (v/v).

By using the lysis solution described above, a detection sample can be prepared easily in a short time without generally conducted extraction and purification of nucleic acid using a commercial purification kit or the like.

The mixing ratio of the lymph node cells to the lysis solution is not particularly limited. About 0.0001 to 0.005 mL of the lysis solution can be added to and mixed with 1 mg of the sample. This mixing, though not particularly limited, can be carried out, for example, at room temperature for such a time as to mix the cells with the lysis solution sufficiently.

After the lymph node cells are mixed with the lysis solution, the cells in the mixture are preferably disrupted. The method of disrupting the cells includes homogenization with a homogenizer and a freezing and thawing method. The homogenizer that can be used is one conventionally used in the art and includes, for example, a Waring blender, a Potter-Elvehjem homogenizer, a polytron homogenizer, a Dounce homogenizer, a French press and an ultrasonic disintegrator. Conditions for disruption are suitably established depending on the method and apparatus used and may be those used usually in the art.

A disruption solution of the cells disrupted by the method described above can be partially purified by usual purification methods such as centrifugation, filtration and column chromatography, thereby preparing a detection sample. Depending on the state of the detection sample, the solution may be further purified by a nucleic acid extraction method.

For detection of the marker of the present invention that can be contained in the detection sample thus obtained, it is preferable that the sample is subjected to nucleic acid amplification in a reaction solution prepared by adding primers capable of detecting the marker, an enzyme having a reverse transcription activity, and a DNA polymerase, followed by detecting the amplified cDNA. The nucleic acid amplification method is not particularly limited, and methods known in the art, such as PCR and LAMP, can be used. Because the marker is RNA, nucleic acid amplification methods involving a reverse transcription reaction prior to the nucleic acid amplification (for example, RT-PCR and RT-LAMP) can be used. By using such nucleic acid amplification methods, cDNA is synthesized based on the marker mRNA as a template, and the obtained cDNA can then serve as a template to advance the nucleic acid amplification reaction.

Conditions for the reverse transcription reaction and nucleic acid amplification reaction can vary suitably depending on the primer sequence and the cDNA sequence as a template corresponding to the marker of the invention. Conditions usable for the reverse transcription reaction and nucleic acid amplification reaction are those described in, for example, Sambrook, J. et al. (1989) Molecular Cloning: A Laboratory Manual (2nd ed.), Cold Spring Harbor Laboratory Press, New York.

The sequence of the primer for detecting the marker is not particularly limited insofar as it is a polynucleotide capable of amplifying the cDNA corresponding to the marker. The primer is preferably 5 to 100 nucleotides in length, more preferably 10 to 50 nucleotides in length. The primer can be produced by the nucleic acid synthesis method known in the art.

The primer may have mutations (substitution, deletion, insertion, addition etc.) of one or more nucleotides insofar as it has a primer function. The "primer function" is a function for the primer to serve as an origin of extension reaction in nucleic acid amplification by hybridizing with the cDNA corresponding to the marker, for example, cDNA synthesized based on the marker, or a chain complementary to the cDNA. The polynucleotide with mutations has preferably at least 60%, more preferably at least 80%, complementarity to its hybridizing region. For allowing this polynucleotide to function as a primer, preferably at least 3 bases in the 3'-end of the polynucleotide, more preferably at least 5 bases in the 3'-end of the polynucleotide, are completely complementary to the marker.

The primer preferably consists of:

(a) a polynucleotide having a sequence set forth in any of SEQ ID NOs 1 to 12, or (b) a polynucleotide having a mutated nucleotide sequence of the polynucleotide (a) with substitution, deletion, insertion or addition of at least one nucleotide and having a primer function in a nucleic acid amplification reaction.

The primers described above can be used as a primer set consisting of a combination of first and second primers (forward and reverse primers) that can, by nucleic acid amplification, amplify a cDNA corresponding to the marker of the present invention. In this case, the primer set includes, for example, a primer set comprising a first primer selected from the group consisting of:

(a) a polynucleotide having a sequence set forth in SEQ ID NO 1, and (b) a polynucleotide having a mutated nucleotide sequence of the polynucleotide (a) with substitution, deletion, insertion or addition of at least one nucleotide and having a primer function in a nucleic acid amplification reaction; and a second primer selected from the group consisting of:

(c) a polynucleotide having a sequence set forth in SEQ ID NO 2, and (d) a polynucleotide having a mutated nucleotide sequence of the polynucleotide (c) with substitution, deletion, insertion or addition of at least one nucleotide and having a primer function in a nucleic acid amplification reaction.

Another example is a primer set comprising a first primer selected from the group consisting of:

(e) a polynucleotide having a sequence set forth in SEQ ID NO 3, and (f) a polynucleotide having a mutated nucleotide sequence of the polynucleotide (e) with substitution, deletion, insertion or addition of at least one nucleotide and having a primer function in a nucleic acid amplification reaction; and a second primer selected from the group consisting of:

(g) a polynucleotide having a sequence set forth in SEQ ID NO 4, and (h) a polynucleotide having a mutated nucleotide sequence of the polynucleotide (g) with substitution, deletion, insertion or addition of at least one nucleotide and having a primer function in a nucleic acid amplification reaction.

Another example is a primer set comprising a first primer selected from the group consisting of:

(i) a polynucleotide having a sequence set forth in SEQ ID NO 5, and (j) a polynucleotide having a mutated nucleotide sequence of the polynucleotide (i) with substitution, deletion, insertion or addition of at least one nucleotide and having a primer function in a nucleic acid amplification reaction; and a second primer selected from the group consisting of:

(k) a polynucleotide having a sequence set forth in SEQ ID NO 6, and (l) a polynucleotide having a mutated nucleotide sequence of the polynucleotide (k) with substitution, deletion, insertion or addition of at least one nucleotide and having a primer function in a nucleic acid amplification reaction.

Another example is a primer set comprising a first primer selected from the group consisting of:

(m) a polynucleotide having a sequence set forth in SEQ ID NO 7, and (n) a polynucleotide having a sequence of the polynucleotide (m) with substitution, deletion, insertion or addition of at least one nucleotide and having a primer function in a nucleic acid amplification reaction; and a second primer selected from the group consisting of:

(o) a polynucleotide having a sequence set forth in SEQ ID NO 8, and (p) a polynucleotide having a mutated nucleotide sequence of the polynucleotide (o) with substitution, deletion, insertion or addition of at least one nucleotide and having a primer function in a nucleic acid amplification reaction.

Another example is a primer set comprising a first primer selected from the group consisting of:

(q) a polynucleotide having a sequence set forth in SEQ ID NO 9, and (r) a polynucleotide having a mutated nucleotide sequence of the polynucleotide (q) with substitution, deletion, insertion or addition of at least one nucleotide and having a primer function in a nucleic acid amplification reaction; and a second primer selected from the group consisting of:

(s) a polynucleotide having a sequence set forth in SEQ ID NO 10, and (t) a polynucleotide having a mutated nucleotide sequence of the polynucleotide (s) with substitution, deletion, insertion or addition of at least one nucleotide and having a primer function in a nucleic acid amplification reaction.

Another example is a primer set comprising a first primer selected from the group consisting of:

(u) a polynucleotide having a sequence set forth in SEQ ID NO 11, and (v) a polynucleotide having a mutated nucleotide sequence of the polynucleotide (u) with substitution, deletion, insertion or addition of at least one nucleotide and having a primer function in a nucleic acid amplification reaction; and a second primer selected from the group consisting of:

(w) a polynucleotide having a sequence set forth in SEQ ID NO 12, and (x) a polynucleotide having a mutated nucleotide sequence of the polynucleotide (w) with substitution, deletion, insertion or addition of at least one nucleotide and having a primer function in a nucleic acid amplification reaction.

The primer may be modified by techniques ordinarily used in the art. Labeling of the primer can be conducted using a radioisotope element or a nonradioactive molecule. The radioisotope used includes 32P, 33P, 35S, 3H and 125I. The nonradioactive molecule is selected from the group consisting of ligands such as biotin, avidin, streptavidin and digoxigenin; haptens; dyes; and luminescent reagents such as radioluminescent, chemiluminescent, bioluminescent, fluorescent or phosphorescent reagents.

The enzyme having a reverse transcription activity and DNA polymerase may be those well known in the art. The enzyme having a reverse transcription activity includes AMV (Avian Myeloblastosis Virus) reverse transcriptase, M-MLV (Molony Murine Leukemia Virus) reverse transcriptase, etc. The DNA polymerase that can be used includes Taq DNA polymerase, Pfu DNA polymerase, T4 DNA polymerase and Bst DNA polymerase.

The marker can be detected by measuring a product produced by the nucleic acid amplification described above. For example, the marker can be detected by detecting the amplified cDNA. Detection of the amplified cDNA can be carried out by mixing a fluorescent intercalator such as ethidium bromide or SYBR Green with the reaction solution to fluorescence-stain the cDNA in the reaction solution and measuring the fluorescence intensity of the reaction solution. Alternatively, the marker can be quantified by previously adding the fluorescent intercalator to the reaction solution and then measuring the fluorescence intensity of the reaction solution in real time.

When magnesium pyrophosphate is produced as a byproduct accompanying cDNA amplification, the cDNA can be detected by detecting this byproduct. Because this magnesium pyrophosphate is insoluble, the reaction solution turns turbid as magnesium pyrophosphate is increased. Accordingly, the cDNA can be detected by optical measurement (for example, turbidity measurement, absorbance determination etc.) of the reaction solution. The marker can also be quantified by optical measurement in real time.

On the basis of the detection result of the marker, the lymph node metastasis of stomach cancer can be judged.

The marker in an embodiment of the present invention may be recognized in an insignificant amount not only in cancer cells but also in normal cells. In such cases, the lymph node metastasis of stomach cancer is judged preferably by comparing the detection result of the marker with a predetermined threshold value.

For example, when the marker is detected in real time by RT-PCR, the number of PCR cycles repeated until predetermined fluorescence intensity or turbidity is reached is determined, and this measured value is compared with the corresponding threshold value, whereby the lymph node metastasis of stomach cancer can be detected. Alternatively, the fluorescence intensity and turbidity in a predetermined number of cycles is measured and this measured value is compared with the corresponding threshold value, whereby the lymph node metastasis of stomach cancer can be detected.

For example, when the marker is detected in real time by RT-LAMP, the time having elapsed until predetermined fluorescence intensity or turbidity is reached is determined, and this measured value is compared with the corresponding threshold value, whereby the lymph node metastasis of stomach cancer can be detected. Alternatively, the fluorescence intensity and turbidity after the lapse of a predetermined time is measured and this measured value is compared with the corresponding threshold value, whereby the lymph node metastasis of stomach cancer can be detected. By establishing a plurality of threshold values, the lymph node metastasis of stomach cancer can be detected in multiple stages such as "most positive", "positive" and "negative".

The threshold value can be established so as to be not higher than a value corresponding to the amount of the marker contained in a biological sample (positive sample) confirmed to contain cancer cells and to be higher than a value corresponding to the amount of the marker contained in a biological sample (negative sample) confirmed not to contain cancer cells. It is preferable that a value corresponding to the amount of the marker in a plurality of positive samples is measured, while a value corresponding to the amount of the marker in a plurality of negative samples is measured, and on the basis of these measurement results, a value capable of distinguishing the positive samples from the negative samples with the highest probability is established as a threshold value.

Microarray technology can also be used in detection of the marker. Specifically, a polynucleotide probe (hereinafter referred to simply as "probe") complementary to the cDNA corresponding to the marker is immobilized on a solid phase. A cDNA-containing sample obtained by reverse transcription reaction from the marker in a detection sample is added to the solid phase, thereby capturing the cDNA with the probe. A fluorescent intercalator is added thereto, thus fluorescence-staining a hybrid between the probe and cDNA, and the fluorescence intensity is detected. From the detection result of the fluorescence intensity, the marker can be quantified or the presence or absence of the marker can be judged. When the probe is shorter than the cDNA, another probe to hybridize with that region of the cDNA with which the above probe does not hybridize can be added to enhance the fluorescence signal.

Alternatively, a probe corresponding to the marker is immobilized on a solid phase, to form a hybrid between the marker and the probe, and this hybrid may be detected to detect the marker.

The probe can be designed and produced in the same method as described for the primer described above. The probe used can be one that has the same sequence as that of the above primer.

Whether or not the marker occurs in excess in a sample can be judged by using any of the methods described above. When it is judged that the marker occurs in excess in the sample, it is judged that stomach cancer-derived cancer cells have metastasized in lymph nodes in question.

On the basis of the detection result of at least one of 6 markers in an embodiment of the present invention, the lymph node metastasis of stomach cancer can be judged. By combining two or more detection results of 6 markers in the embodiments of the present invention, higher-accuracy detection of lymph node metastasis can be accomplished. Further, the detection results of 6 markers in an embodiment of the present invention are combined with detection results of other markers (for example, CEA and CK20 that are conventional markers of lymph node metastasis of stomach cancer), whereby higher-accuracy detection of lymph node metastasis can be accomplished.

Reagents, etc., for detection of the marker in an embodiment of the present invention can be provided in the form of a reagent kit. The kit comprises at least the above-mentioned primers, an enzyme having a reverse transcription activity, a DNA polymerase, and dNTPs. This kit preferably comprises a buffer giving suitable conditions to the enzyme reaction.

In this specification, the phrase "detecting the marker" includes detection of the whole region of the mRNA that is the marker but also detection of a partial region thereof. In an embodiment of the present invention, the cDNA corresponding to a partial region of the marker is preferably amplified and detected. In this case, the detected region of the cDNA is preferably 1 to 500 nucleotides longer, more preferably 50 to 500 nucleotides longer, than the length of the primer. When the primer set described above is used, the amplified region of the cDNA is preferably 1 to 500 nucleotides longer, more preferably 50 to 500 nucleotides longer, than the total length of the first primer and the second primer.

EXAMPLES

Example 1

Markers capable of detecting the lymph node metastasis of stomach cancer were investigated. First, stomach-related gene expression libraries were selected from human gene expression libraries registered in a public database, and from this database, the top 58 genes expressed in high levels in the stomach but expressed in low levels in lymph nodes were selected in descending order of expression level in the stomach. Proteins corresponding to these genes are shown in Tables 1 and 2.

Then, 58 primer sets were designed to detect 58 kinds of mRNA sequences, each of which encodes these protein-coding genes (these 58 mRNAs are referred to hereinafter as marker candidates) RNAs were extracted from 10 lymph nodes (positive lymph nodes) histologically recognized to undergo lymph node metastasis and 10 lymph nodes (negative lymph nodes) histologically not recognized to undergo lymph node metastasis. The extracted RNAs were then subjected to RT-PCR with the designed 58 primer sets.

First, 4 mL of a lysis solution (200 mM glycine-HCl, 5% Brij35 (polyoxyethylene (35) lauryl ether), 20% DMSO and 0.05% KS-538 (Shin-Etsu Chemical Co.)) was added to each lymph node (about 100 to 300 mg/lymph node) which was then homogenized with a blender. The resulting homogenate was centrifuged at 10,000×g at room temperature for 1 minutes, and RNA was extracted and purified from 400 μl of the supernatant by an RNeasy Mini kit (Catalog No. 74014, manufactured by Qiagen) to give an RNA solution. This RNA solution was measured for its absorbance (λ=280 nm) to confirm its concentration and then diluted to a concentration of 10 ng/μL. The RNA solutions thus prepared from the 10 positive lymph nodes were mixed to prepare a positive sample, and the RNA solutions prepared from the 10 negative lymph nodes were mixed to prepare a negative sample.

The positive sample and negative sample obtained in the manner described above were subjected to real-time RT-PCR with the above-mentioned 58 primer sets in an ABI Real-Time PCR Unit (Prism 7000) to detect the 58 kinds of target mRNAs.

The real-time RT-PCR was carried out using a quantitative RT-PCR kit, that is, a Quanti Tect SYBR Green RT-PCR kit (Catalog No. 204245, manufactured by Qiagen) according to the manufacture's instructions. The composition of the reaction solution and the reaction conditions are as follows.

Reaction Solution:

| | |
|---|---|
| RNase free $H_2O$ | 22.00 μL |
| 2 × Mix | 25.00 μL |
| 100 nM forward primer (final concentration 500 (μM) | 0.25 μL |
| 100 nM reverse primer (final concentration 500 (μM) | 0.25 μL |
| Quanti Tect RT Mix | 0.50 μL |
| Positive sample or negative sample | 2.00 μL |
| Total | 50.00 μL |

Reaction Conditions:

| | |
|---|---|
| 50° C. | 30 minutes |
| 95° C. | 15 minutes |

PCR: 40 Cycles of the Following Process;

| | |
|---|---|
| 94° C. | 15 seconds |
| 53° C. | 30 seconds |
| 72° C. | 30 seconds |

RT-PCR was carried out under the conditions described above, and the negative sample and positive sample were measured respectively for the number of PCR cycles (the number of PCR cycles for the negative sample and the number of PCR cycles for the positive sample) repeated until a certain specific fluorescence intensity was reached, and the difference therebetween ((the number of PCR cycles for the negative sample)−(the number of PCR cycles for the positive sample)) was determined. A larger difference in the number of PCR cycles therebetween indicates lower expression level of the gene in the negative sample and higher expression level thereof in the positive sample, namely, meaning that the gene is expressed in higher level specifically in lymph nodes that have developed metastasis.

The results are shown in Table 1, Table 2, and FIG. 1. Tables 1 and 2 are tables showing the number of PCR cycles for the positive sample (A), the number of PCR cycles for the negative sample (B), and the difference therebetween (B-A). FIG. 1 is a graph with B-A on the ordinate and B on the abscissa. A larger value on the ordinate is indicative of lower expression level of the gene in the negative sample and higher expression level in the positive sample, namely, meaning that the gene is expressed in higher level specifically in lymph nodes that have developed metastasis. A larger number of cycles on the abscissa is indicative of lower expression level of the gene in lymph nodes without stomach cancer metastasis.

Therefore, it can be said that marker candidates showing a relatively large value on the ordinate and a relatively large number of cycles on the abscissa are useful as markers for detecting the lymph node metastasis of stomach cancer.

β-Actin (ACTB) used as a control is known as a protein of a housekeeping gene and expressed in a large amount in many cells. Accordingly, β-Actin is low both in the number of PCR cycles for the negative sample and in the number of PCR cycles for the positive sample.

CEA and CK20 mRNAs that have conventionally been known as markers of lymph node metastasis of stomach cancer show a relatively large value on the ordinate and a relatively large number of cycles on the abscissa and can thus be seen to be expressed in large amounts specifically in tissues that have developed lymph node metastasis.

TABLE 1

| Sample No | Protein Abbreviation | A (Number of PCR Cycles for Positive Sample) | B (Number of PCR Cycles for Negative Sample) | B − A |
|---|---|---|---|---|
| 1 | ZNF45 | 24.835 | 25.825 | 0.99 |
| 2 | QSCN6 | 21.33 | 24.215 | 2.885 |
| 3 | IGFBP4 | 21.715 | 23.075 | 1.36 |
| 4 | DES | 22.885 | 23.425 | 0.54 |
| 5 | COL1A2 | 18.595 | 22.485 | 3.89 |
| 6 | SERPING1 | 18.995 | 20.38 | 1.385 |
| 7 | FHL1 | 22.975 | 23.63 | 0.655 |
| 8 | ZNF499 | 24.22 | 25.355 | 1.135 |
| 9 | CD9 | 23.765 | 26.085 | 2.32 |
| 10 | PDE3A | 25.355 | 26.395 | 1.04 |
| 11 | CDH1 | 22.81 | 26.64 | 3.83 |
| 12 | S100P | 25.08 | 25.445 | 0.365 |
| 13 | LGMN | 20.04 | 20.995 | 0.955 |
| 14 | PARD3 | 25.455 | 27.845 | 2.39 |
| 15 | APOL1 | 21.8 | 24.095 | 2.295 |
| 16 | MCAM | 21.725 | 22.815 | 1.09 |
| 17 | FOSL2 | 20.93 | 22.475 | 1.545 |
| 18 | MUC4 | 27.82 | 36.355 | 8.535 |
| 19 | SERPINH1 | 23.635 | 25.92 | 2.285 |
| 20 | CA2 | 20.805 | 26.84 | 6.035 |
| 21 | NDRG2 | 29.11 | 29.585 | 0.475 |
| 22 | PIGR | 22.71 | 30.69 | 7.98 |
| 23 | PAM | 23.38 | 24.53 | 1.15 |
| 24 | LCMT2 | 25.36 | 25.95 | 0.59 |
| 25 | TM4SF1 | 20.615 | 23.06 | 2.445 |
| 26 | COL6A2 | 20.58 | 22.695 | 2.115 |
| 27 | MYL9 | 21.115 | 22.55 | 1.435 |
| 28 | COL1A1 | 19.185 | 24.365 | 5.18 |
| 29 | AGR2 | 17.15 | 29.025 | 11.875 |
| 30 | REG3A | 31.84 | 32.1 | 0.26 |

TABLE 2

| Sample No | Protein Abbreviation | A (Number of PCR Cycles for Positive Sample) | B (Number of PCR Cycles for Negative Sample) | B − A |
|---|---|---|---|---|
| 31 | EPS8L3 | 28.345 | 33.51 | 5.165 |
| 32 | REG1A | 28.685 | 33.775 | 5.09 |
| 33 | ALDH1A1 | 19.75 | 23.24 | 3.49 |
| 34 | REG4 | 20.18 | 29.325 | 9.145 |

TABLE 2-continued

| Sample No | Protein Abbreviation | A (Number of PCR Cycles for Positive Sample) | B (Number of PCR Cycles for Negative Sample) | B − A |
|---|---|---|---|---|
| 35 | CEBPA | 24.23 | 26.575 | 2.345 |
| 36 | ACTA2 | 19.255 | 20.24 | 0.985 |
| 37 | MUC6 | 26.76 | 29.7 | 2.94 |
| 38 | TSPAN8 | 20.25 | 27.91 | 7.66 |
| 39 | MUC1 | 20.58 | 29.825 | 9.245 |
| 40 | ALDH3A1 | 26.76 | 31.825 | 5.065 |
| 41 | TFF1 | 18.51 | 36.55 | 18.04 |
| 42 | CLDN18 | 26.805 | 33.725 | 6.92 |
| 43 | CEACAM5 | 19.53 | 39.21 | 19.68 |
| 44 | IFITM3 | 18.605 | 19.63 | 1.025 |
| 45 | CNN1 | 23.525 | 25.275 | 1.75 |
| 46 | POF1B | 23.62 | 27.745 | 4.125 |
| 47 | GPX2 | 22.57 | 28.045 | 5.475 |
| 48 | GDDR | 27.105 | 31.565 | 4.46 |
| 49 | PRSS8 | 22.92 | 34.04 | 11.12 |
| 50 | MUC17 | 25.6 | 35.315 | 9.715 |
| 51 | CK19 | 20.025 | 32.715 | 12.69 |
| 52 | CK18 | 19.24 | 23.83 | 4.59 |
| 53 | CK20 | 21.115 | 35.65 | 14.535 |
| 54 | CK7 | 28.815 | 32.605 | 3.79 |
| 55 | CK8 | 19.635 | 27.375 | 7.74 |
| 56 | CK14 | 24.845 | 29.78 | 4.935 |
| 57 | MUC2 | 27.725 | 36.69 | 8.965 |
| 58 | COL3A1 | 19.46 | 23.885 | 4.425 |
| Control | ACTB | 14.445 | 15.63 | 1.185 |

From the results shown above, mRNAs of genes encoding the 11 proteins indicated in black circles in FIG. 1 were considered highly useful as markers of lymph mode metastasis. These 11 marker candidates contain marker candidates such as TFF1, AGR2, PRSS8, MUC1, MUC2, MUC4, MUC17 and REG4 that are not known as markers of lymph node metastasis of stomach cancer, in addition to CEA and CK20 that have conventionally been known as markers of lymph node metastasis of stomach cancer.

Example 2

Then, the 11 marker candidates (TFF1, AGR2, PRSS8, MUC1, MUC2, MUC4, MUC17, REG4, CEA, CK19, CK20) shown in Example 1 were examined in more detail for their usefulness as markers of lymph node metastasis of stomach cancer.

From 9 lymph nodes histologically recognized to have metastasis of stomach cancer, 9 RNA solution samples (positive samples) were prepared. From 10 lymph nodes histologically recognized to be free of metastasis of stomach cancer, 10 RNA solution samples (negative samples) were prepared. The 9 positive samples and 10 negative samples were subjected respectively to real-time RT-PCR, thereby detecting mRNAs of genes encoding the 11 proteins mentioned above.

The method of preparing the RNA solutions, and the conditions for RT-PCR, are the same as in Example 1. Primers used in RT-PCR for detecting the 11 marker candidates are those primers having sequences of SEQ ID NOs 1 to 22 respectively, as shown in Table 3 below.

As the control, an mRNA for β-actin (ACTB), that is, a protein of a housekeeping gene, was detected. Primers used in RT-PCR for detecting the mRNA for β-actin (ACTB) are those primers having sequences of SEQ ID NOs 23 and 24 respectively, as shown in Table 3 below.

TABLE 3

| Protein Abbreviation | First Primer | SEQ ID NO | Second Primer | SEQ ID NO |
|---|---|---|---|---|
| TFF1 | CCCTGGTGCTTCTATCCTAA | 1 | CAGATCCCTGCAGAAGTGTC | 2 |
| AGR2 | ATTCTTGCTCCTTGTGGCCCT | 3 | ATGAGTTGGTCACCCCAACCTC | 4 |
| PRSS8 | TTCCCTGATGGCCTTTGGA | 5 | CCCAAAAAGCACACCCAGAAG | 6 |
| MUC1 | CCCAGTCTCCTTTCCTCCTGCT | 7 | GCCGAAGTCTCCTTTTCTCCAC | 8 |
| MUC2 | CCATGTATCCTGATGTTCCCATTG | 13 | GCACTGAACGTTGATCTCGTAGTTG | 14 |
| MUC4 | CCACCAACTTCATCGCCTTTG | 9 | CGTCTTCATGGTCAGGCTGAAA | 10 |
| MUC17 | AGGCCTCAGGTAATGACGACA | 11 | AGTTCCCATGGAAGGCTCTCA | 12 |
| REG4 | CTTCCTGTGCAAGTACCGACCA | 15 | TGAGCAGATTTAGCCAGGCTAGC | 16 |
| CEACAM5 | AGACAATCACAGTCTCTGCGGA | 17 | ATCCTTGTCCTCCACGGGTT | 18 |
| CK19 | CAGATCGAAGGCCTGAAGGA | 19 | CTTGGCCCCTCAGCGTACT | 20 |
| CK20 | CATTGACAGTGTTGCCCAGATG | 21 | AAAGACCTAGCTCTCCTCAAAAAGG | 22 |
| ACTB | TCCTCACCCTGAAGTACCCCAT | 23 | AGCCACACGCAGCTCATTGTAG | 24 |

Figure 2:
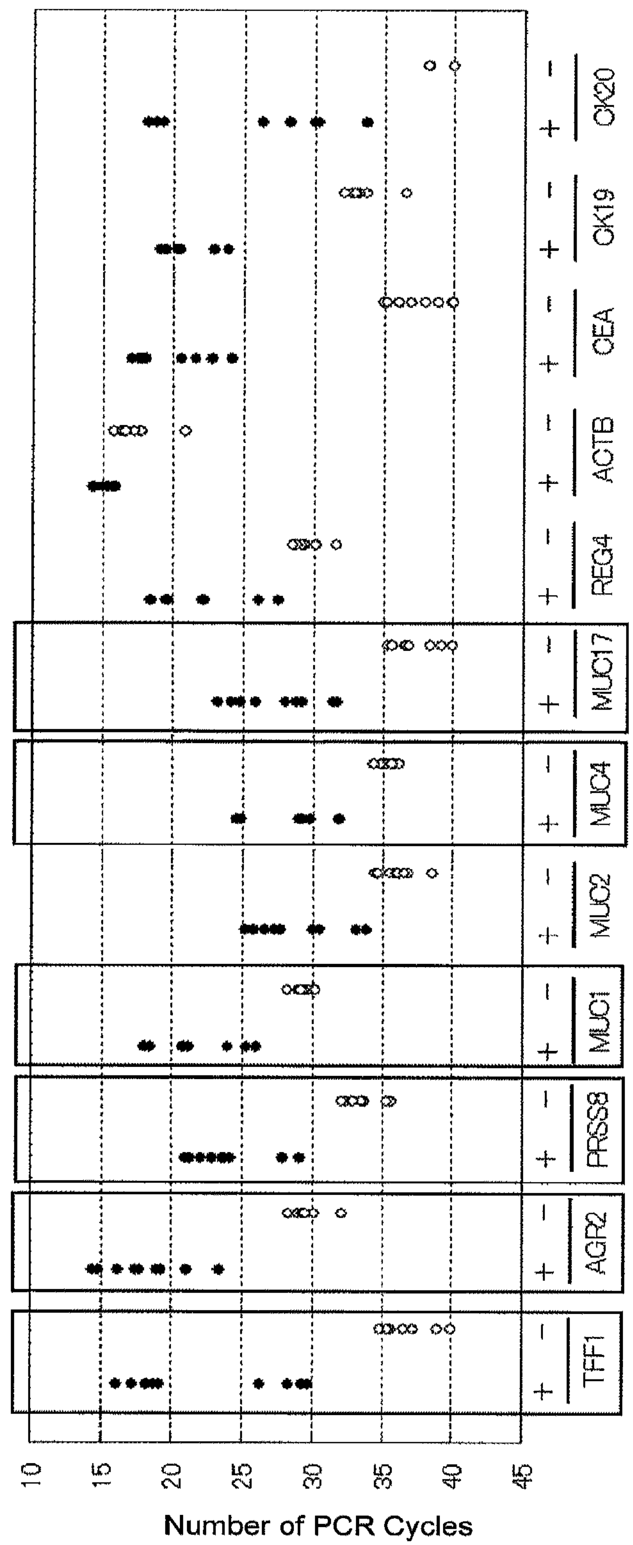
FIG. 2 is the number of PCT cycles (Ct) repeated until a specific fluorescence intensity was reached during RT-PCR amplification of cDNAs for 11 marker candidates (TFF1, AGR2, PRSS8, MUC1, MUC2, MUC4, MUC17, REG4, CEA, CK19, and CK20) in lymph node samples from patients confirmed to have lymph node metastasis and in lymph node samples from patients not recognized to have metastasis.

The number of PCR cycles in these real-time RT-PCR repeated until a certain specific fluorescence intensity was reached, and the results are shown in FIG. 2. In FIG. 2, the number of PCR cycles repeated until a certain specific intensity was reached with the positive or negative samples is shown on the ordinate. "+" indicates measurement results where the positive samples were used, and "−" indicates measurement results where the negative samples were used.

From the results shown in FIG. 2, it was found that among the 11 marker candidates shown in Example 1, both mRNAs of CEA and CK20 known conventionally as markers of lymph node metastasis of stomach cancer were amplified with a smaller number of cycles in the positive samples and amplified with a larger number of cycles in the negative samples. Then, a clear difference was observed between the number of cycles where the positive samples were used and the number of cycles where the negative samples were used.

It was found that among the 11 marker candidates shown in Example 1, TFF1, AGR2, PRSS8, MUC1, MUC2, MUC4, MUC17 and REG4 were amplified with a smaller number of cycles in the positive samples and amplified with a larger number of cycles in the negative samples. With respect to 6 marker candidates TFF1, AGR2, PRSS8, MUC1, MUC4 and MUC17, similar to CEA and CK20 conventionally known as markers of lymph node metastasis of stomach cancer, a clear difference was observed between the number of cycles where the positive samples were used and the number of cycles where the negative samples were used. From the foregoing, it was revealed that mRNAs encoding TFF1, AGR2, PRSS8, MUC1, MUC4 and MUC17 not known as markers of lymph node metastasis of stomach cancer are useful as markers of lymph node metastasis of stomach cancer.

With respect to CK19, similar to CEA and CK20 known conventionally as markers of lymph node metastasis of stomach cancer, among the 11 marker candidates shown in Example 1, a clear difference was observed between the number of cycles where the positive samples were used and the number of cycles where the negative samples were used.

From the results in FIG. 2, it was found that 6 marker candidates TFF1, AGR2, PRSS8, MUC1, MUC4 and MUC17 can clearly distinguish between the positive samples and negative samples used in this example by establishing specific threshold values for the number of PCR cycles in detection of their RNAs. That is, it was found that by establishing specific threshold values for the number of PCR cycles in detection of their RNAs, the 6 marker candidates can judge all the positive samples used in this example to be positive and all the negative samples used in this example to be negative.

Specifically, all the positive samples used in this example can be judged to be positive, while all the negative samples used in this example can be judged to be negative, by establishing a threshold value for the number of cycles in the range of 30 to 34 in detection of the mRNA for TFF1.

By establishing a threshold value for the number of cycles in the range of 23 to 28 in detection of the mRNA for AGR2, all the positive samples used in this example can be judged to be positive, while all the negative samples used in this example can be judged to be negative.

By establishing a threshold value for the number of cycles in the range of 29 to 32 in detection of the mRNA for PRSS8, all the positive samples used in this example can be judged to be positive, while all the negative samples used in this example can be judged to be negative.

By establishing a threshold value for the number of cycles in the range of 26 to 28 in detection of the mRNA for MUC1, all the positive samples used in this example can be judged to be positive, while all the negative samples used in this example can be judged to be negative.

By establishing a threshold value for the number of cycles in the range of 32 to 34 in detection of the mRNA for MUC4, all the positive samples used in this example can be judged to be positive, while all the negative samples used in this example can be judged to be negative.

By establishing a threshold value for the number of cycles in the range of 31 to 35 in detection of the mRNA for MUC17, all the positive samples used in this example can be judged to be positive, while all the negative samples used in this example can be judged to be negative.

The mRNA for β-actin (ACTB), that is, a protein of a housekeeping gene, was detected with a similar number of cycles with any of the positive and negative samples, and it was thus confirmed that the used samples were not those significantly different from one another in nucleic acid concentration.

By an experiment of electrophoresis with the positive samples after the reaction, it was confirmed that amplification of DNAs detected in the positive samples in this example was not due to unspecific reaction of primer dimers etc. (not shown).

From the foregoing, mRNAs encoding TFF1, AGR2, PRSS8, MUC1, MUC4 and MUC17 conventionally not known as markers of lymph node metastasis of stomach cancer were newly found to be useful as markers of lymph node metastasis of stomach cancer. As shown in Table 4 below, sequences of the respective mRNAs are as shown in SEQ ID NOs 25 to 30 respectively. These sequences can be obtained under the accession numbers shown in Table 4 below, from Genbank (www.ncbi.nlm.nih.gov/Genbank/index.html).

TABLE 4

| Protein Abbreviation | SEQ ID NO | Genbank Accession Number |
|---|---|---|
| TFF1 | 25 | NM_003225 |
| AGR2 | 26 | NM_006408 |
| PRSS8 | 27 | NM_002773 |
| MUC1 | 28 | NM_002456 |
| MUC4 | 29 | NM_018406 |
| MUC17 | 30 | NM_001040105 |

By combining two or more detection results of the novel 6 markers, higher-accuracy detection of lymph node metastasis can be accomplished. Further, the detection results of the novel 6 markers are combined with detection results of other markers whereby higher-accuracy detection of lymph node metastasis can be accomplished. The other markers include, for example, CK19, as well as CEA and CK20 that are conventional markers of lymph node metastasis of stomach cancer.

What is claimed is:

1. A method for determining lymph node metastasis of stomach cancer, comprising: preparing a detection sample from a lymph node obtained from a human patient with stomach cancer, assaying said detection sample to obtain a level of mRNA of anterior gradient 2 homolog to detect lymph node metastasis of stomach cancer; and determining the presence of lymph node metastasis of stomach cancer when the level of mRNA of anterior gradient 2 homolog occurs in excess in comparison to lymph nodes which are free of metastasis of stomach cancer.

2. A method of claim 1, wherein the anterior gradient 2 homolog comprises a polynucleotide selected from the group consisting of: (a) the polynucleotide sequence of SEQ ID NO: 3 and (b) the polynucleotide having at least 85% sequence identity with SEQ ID NO: 3, wherein at least 3 bases in the 3'-end of the polynucleotide are complementary to the anterior gradient 2 homolog.

3. The method according to claim 1, wherein the assaying step is performed by conducting a reverse transcription reaction and nucleic acid amplification reaction using the detection sample, an enzyme having a reverse transcription activity, a DNA polymerase and primers for amplification of the anterior gradient 2 homolog, and measuring a product generated by the amplification to obtain a measured value, and wherein the determining step is performed by detecting whether the anterior gradient 2 homolog occurs in excess based on the measured value.

4. The method according to claim 3, wherein the determining step is performed by comparing the measured value with a measured value of lymph nodes which are free of metastasis of stomach cancer, and detecting whether the anterior gradient 2 homolog occurs in excess based on the comparison.

5. A method for determining the lymph node metastasis of stomach cancer, comprising steps of: preparing a detection sample from a lymph node obtained from a human patient with stomach cancer, assaying said detection sample to obtain a level of mRNA of anterior gradient 2 homolog to detect lymph node metastasis of stomach cancer by using a primer set for detection of anterior gradient 2 homolog, and determining a presence of lymph node metastasis of stomach cancer when the level of mRNA of anterior gradient 2 homolog occurs in excess in comparison to lymph nodes which are free of metastasis of stomach cancer, wherein said primer set for detection of anterior gradient 2 homolog comprises: a polynucleotide selected from the group consisting of: (a) the polynucleotide sequence of SEQ ID NO 3, and (b) the polynucleotide having at least 85% sequence identity with SEQ ID NO: 3, wherein at least 3 bases in the 3'-end of the polynucleotide are complementary to the anterior gradient 2 homolog, and another polynucleotide selected from the group consisting of: (c) the polynucleotide sequence of SEQ ID NO 4, and (d) the polynucleotide having at least 85% sequence identity with SEQ ID NO: 4, wherein at least 3 bases in the 3'-end of the polynucleotide are complementary to the anterior gradient 2 homolog.

6. The method according to claim 5, wherein the assaying step is performed by conducting a reverse transcription reaction and nucleic acid amplification reaction using the detection sample, an enzyme having a reverse transcription activity, a DNA polymerase and the primer set for detecting the anterior gradient 2 homolog, and measuring a product generated by the amplification to obtain a measured value, and wherein the determining step is performed by detecting whether the anterior gradient 2 homolog occurs in excess based on the measured value.

7. The method according to claim 6, wherein the determining step is performed by comparing the level of mRNA of anterior gradient 2 homolog with a measured value of lymph nodes which are free of metastasis of stomach cancer, and detecting whether the anterior gradient 2 homolog occurs in excess based on the comparison.

* * * * *